United States Patent
Kalyanaraman et al.

(10) Patent No.: US 11,352,382 B2
(45) Date of Patent: Jun. 7, 2022

(54) MITO-LONIDAMINE, COMPOSITIONS AND METHODS OF USE

(71) Applicants: THE MEDICAL COLLEGE OF WISCONSIN, INC., Milwaukee, WI (US); AIX-MARSEILLE UNIVERSITE, Marseilles (FR)

(72) Inventors: Balaraman Kalyanaraman, Wauwatosa, WI (US); Micael J. Hardy, Nîmes (FR); Olivier Ouari, Seynod (FR)

(73) Assignees: The Medical College of Wisconsin, Inc., Milwaukee, WI (US); Aix-Marseille Universite, Marseilles (FR)

( * ) Notice: Subject to any disclaimer, the term of this patent is extended or adjusted under 35 U.S.C. 154(b) by 0 days.

(21) Appl. No.: 16/959,975

(22) PCT Filed: Jan. 3, 2019

(86) PCT No.: PCT/US2019/012190
§ 371 (c)(1),
(2) Date: Jul. 2, 2020

(87) PCT Pub. No.: WO2019/136154
PCT Pub. Date: Jul. 11, 2019

(65) Prior Publication Data
US 2021/0061830 A1    Mar. 4, 2021

Related U.S. Application Data

(60) Provisional application No. 62/613,188, filed on Jan. 3, 2018.

(51) Int. Cl.
C07F 9/6503 (2006.01)
A61P 35/04 (2006.01)
C07F 9/6558 (2006.01)

(52) U.S. Cl.
CPC .......... C07F 9/65038 (2013.01); A61P 35/04 (2018.01); C07F 9/65583 (2013.01)

(58) Field of Classification Search
CPC .................. C07F 9/65038; C07F 9/65583
See application file for complete search history.

(56) References Cited

U.S. PATENT DOCUMENTS

| 5,260,327 A * | 11/1993 | Kim .................. A61K 31/11 514/405 |
| 2007/0015771 A1 | 1/2007 | Matteucci et al. |
| 2017/0275313 A1 | 9/2017 | Kalyanaraman et al. |

FOREIGN PATENT DOCUMENTS

| WO | WO-2004/064734 A2 * | 8/2004 |
| WO | 2008145116 | 12/2008 |
| WO | 2015002996 | 1/2015 |

OTHER PUBLICATIONS

Liu et al., ACS Applied Materials & Interfaces (Nov. 24, 2017), 9(50), pp. 43498-43507. (Year: 2017).*
De Lena, et al. Paclitaxel, cisplatin and lonidamine in advanced ovarian cancer A phase II study. Eur J Cancer. 2001; 37(3):364-8.
Di Cosimo et al. Lonidamine: efficacy and safety in clinical trials for the treatment of solid tumors. Drugs Today (Barc). 2003; 39(3):157-74.
Floridi, et al. Effect of lonidamine on the energy metabolism of Ehrlich ascites tumor cells. Cancer Res 41(11 Pt 1):4661-6, 1981.
Floridi, et al. Enhancement of doxorubicin content by the antitumor drug lonidamine in resistant Ehrlich ascites tumor cells through modulation of energy metabolism. Biochem Pharmacol 56:841-9, 1998.
Guo, et al. Inhibition of Mitochondrial Complex II by the Anticancer Agent Lonidamine. J Biol Chem. 2016; 291:42-57.
Milane, et al. Therapeutic Efficacy and Safety of Paclitaxel/Lonidamine Loaded EGFR-Targeted Nanoparticles for the Treatment of Multi-Drug Resistant Cancer. PLoS ONE 2011; 6(9): e24075.
Natali et al. Inhibition of aerobic glycolysis in normal and neoplastic lymphoid cells induced by Lonidamine [1-(2,4-dichlorobenzyl)-l-H-indazol-3-carboxylicacid]. Oncology. 1984;41 Suppl 1:7-14.
PCT/US2019/012190—International Search Report and Written Opinion, dated Feb. 27, 2019.

* cited by examiner

*Primary Examiner* — Laura L Stockton
(74) *Attorney, Agent, or Firm* — Quarles & Brady LLP

(57) ABSTRACT

The present invention relates to mito-lonidamine compounds, compositions and methods of use in the treatment of cancer.

19 Claims, 27 Drawing Sheets

A
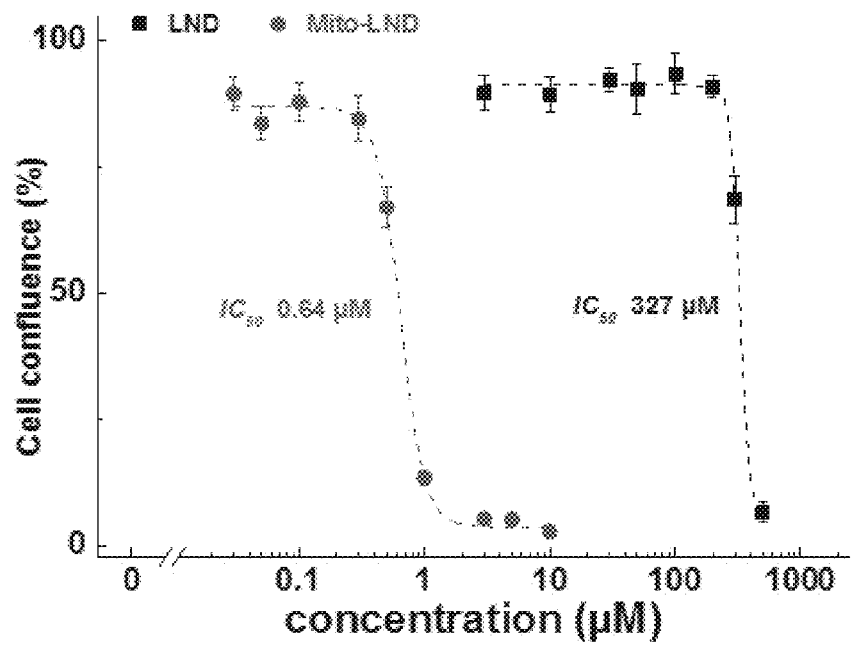
B
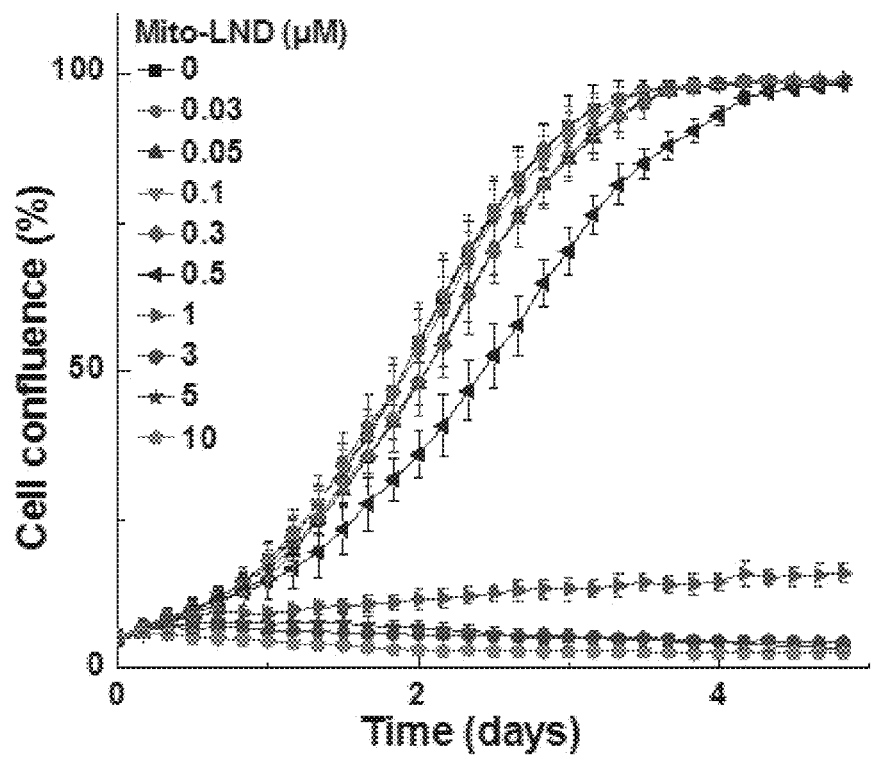
FIGS. 6A-6C

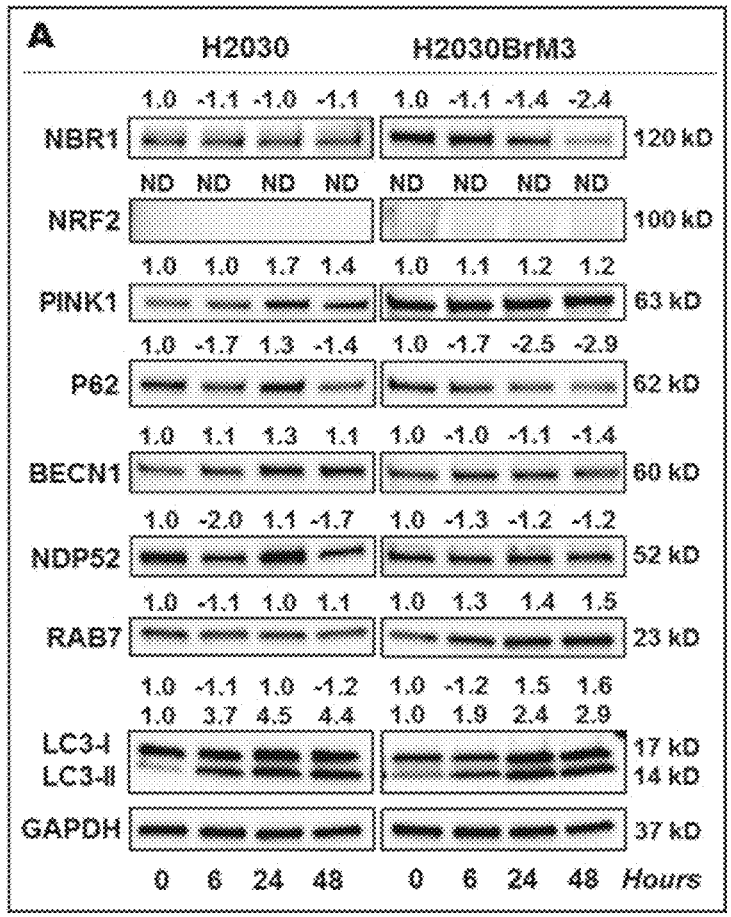
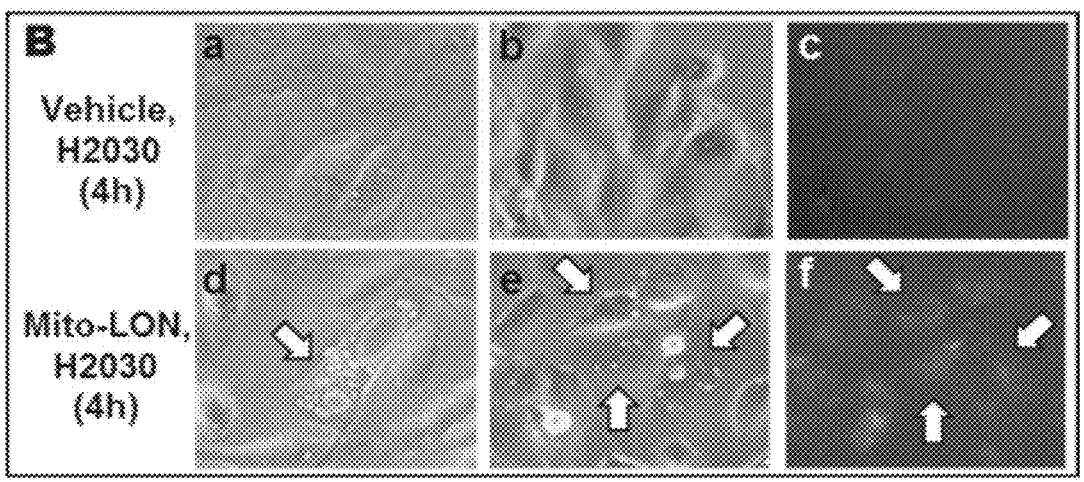
FIGS. 19A-19C

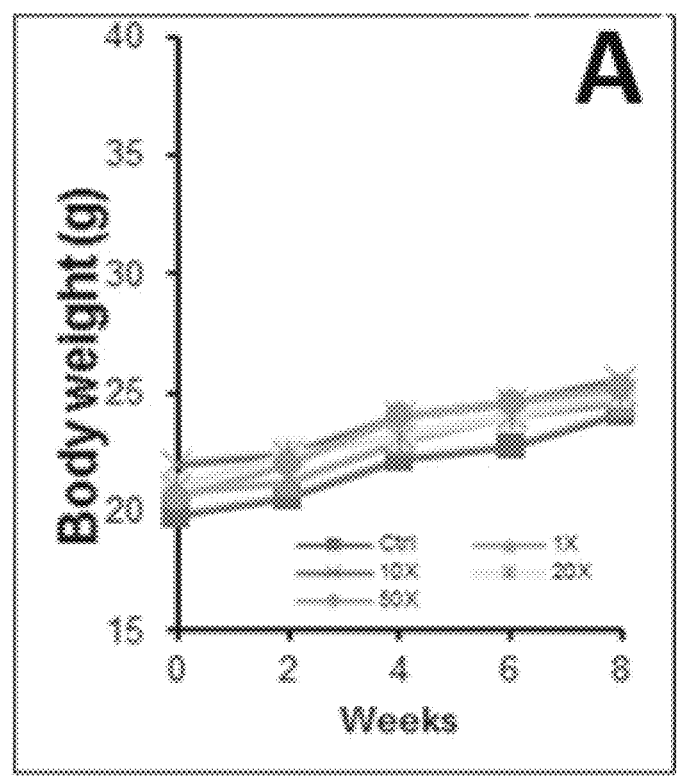
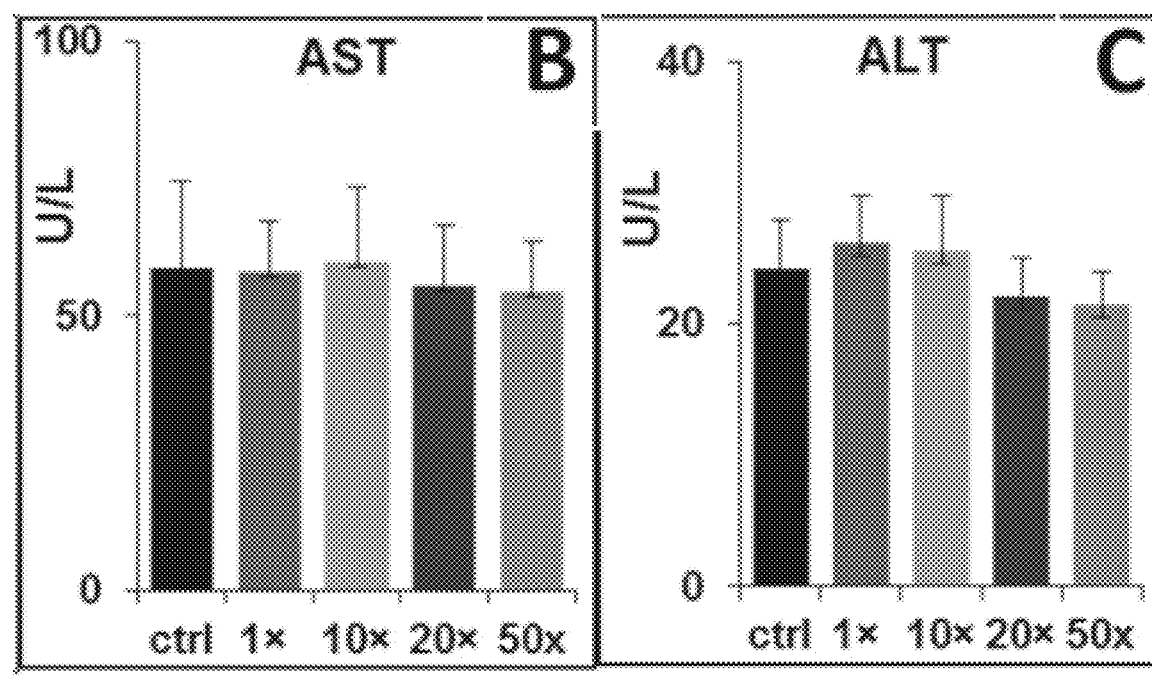
FIGS. 22A-22C

MITO-LONIDAMINE, COMPOSITIONS AND METHODS OF USE

CROSS-REFERENCE TO RELATED APPLICATIONS

This application claims priority to U.S. Provisional Application No. 62/613,188 filed on Jan. 3, 2018, the contents of which are incorporated by reference in its entirety.

STATEMENT REGARDING FEDERALLY SPONSORED RESEARCH

N/A

BACKGROUND OF THE INVENTION

The field of the invention is related to compounds for treatment of cancer and methods of use. More particularly, the invention relates to mito-lonidamine compounds and compositions.

Cancer is one of the leading causes of morbidity and mortality worldwide, with approximately 14 million new cases in 2012. Cancer is the second leading cause of death globally, and was responsible for 8.8 million deaths in 2015. Globally, nearly 1 in 6 deaths is due to cancer. Lung cancer is the leading cause of cancer death in the United States.

Lonidamine (also known as LND or LON: 1-(2,4-dichlorobenzyl)-1H-indazole-3-carboxylic acid) has been used in combination with conventional chemotherapeutics (paclitaxel, cis-platin, doxorubicin) and with radiation therapy to treat a wide variety of cancers (breast, ovarian, prostate and brain) (See De Lena M, Lorusso V, Latorre A, Fanizza G, Gargano G, Caporusso L, Guida M, Catino A, Crucitta E, Sambiasi D, Mazzei A. Paclitaxel, cisplatin and lonidamine in advanced ovarian cancer. A phase II study. Eur J Cancer 37:364-8, 2001, Di Cosimo S, Ferretti G, Papaldo P, Carlini P, Fabi A, Cognetti F. Lonidamine: efficacy and safety in clinical trials for the treatment of solid tumors. Drugs Today (Barc) 39:157-74, 2003). LND exhibits a large margin of safety in humans (See Id.). Although the actual mechanism of action is still under active investigation, most studies suggest that LND inhibits glycolysis in cancer cells, thereby restricting the central energy metabolic pathway (e.g., Warburg mechanism) utilized by cancer cells (See, Floridi A, Bruno T, Miccadei S, Fanciulli M, Federico A, Paggi M G. Enhancement of doxorubicin content by the antitumor drug lonidamine in resistant Ehrlich ascites tumor cells through modulation of energy metabolism. Biochem Pharmacol 56:841-9, 1998; Natali P G, Salsano F, Viora M, Nista A, Malorni W, Marolla A, De Martino C. Inhibition of aerobic glycolysis in normal and neoplastic lymphoid cells induced by Lonidamine [1-(2,4-dichlorobenzyl)-I-H-indazol-3-carboxylic acid]. Oncology 41 Suppl 1:7-14, 1984). LND was initially thought to inhibit the phosphorylation of glucose to glucose 6-phosphate which is catalyzed by hexokinases (HKs), in particular, hexokinase II associated with the mitochondrial membrane (See Floridi A, Paggi M G, D'Atri S, De Martino C, Marcante M L, Silvestrini B, Caputo A. Effect of lonidamine on the energy metabolism of Ehrlich ascites tumor cells. Cancer Res 41(11 Pt 1):4661-6, 1981). LND also was shown to enhance intracellular acidification (enhanced lactate levels) caused by inhibition of monocarboxylic acid transporter (MCT-1), thus preventing the efflux of lactate from cells. A more recent report suggests that LND inhibits mitochondrial complex II enzyme present in the mitochondrial respiratory chain (Guo L, Shestov A A, Worth A J, Nath K, Nelson D S, Leeper D B, Glickson J D, Blair I A. Inhibition of Mitochondrial Complex II by the Anticancer Agent Lonidamine. J Biol Chem 291:42-57, 2016). Prior groups have enhanced the efficacy of LND by targeted delivery systems involving nanoparticles (See, Milane L, Duan Z F, Amiji M. Pharmacokinetics and biodistribution of lonidamine/paclitaxel loaded, EGFR-targeted nanoparticles in an orthotopic animal model of multi-drug resistant breast cancer. Nanomedicine 7:435-44, 2011; Milane L, Duan Z, Amiji M. Therapeutic efficacy and safety of paclitaxel/lonidamine loaded EGFR-targeted nanoparticles for the treatment of multi-drug resistant cancer. PLoS One 6(9): e24075, 2011). Tumor suppressive effects of LND were markedly improved using EGF receptor-targeting nanoparticles (Milane et al. 2011). Using the nanoparticle carrier, the efficacy of LND antitumor effects was enhanced by about 100-fold (Milane et al. 2011).

However, there is still a need for improved and enhanced efficacy of LND for cancer treatment.

SUMMARY OF THE INVENTION

The present invention overcomes the aforementioned drawbacks by providing a mito-lonidamine which has increased efficacy in inhibiting tumor growth and metastasis.

In one aspect, the present invention provides a mito-lonidamine compound of formula I:

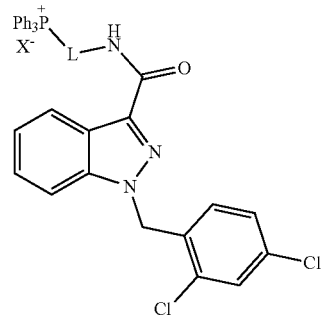

wherein L is a linker selected from an C2-C20 alkyl, an amino acid, benzyl, ramificiation of the alkyl side chain, a C2-C20 alkene or PEG, n is a positive integer selected from 2-20, and X is any halogen, 2,2,2-trifluoroacetic acid (TFA) or acetic acid.

In another aspect, the present invention provides a mito-lonidamine compound of formula Ia

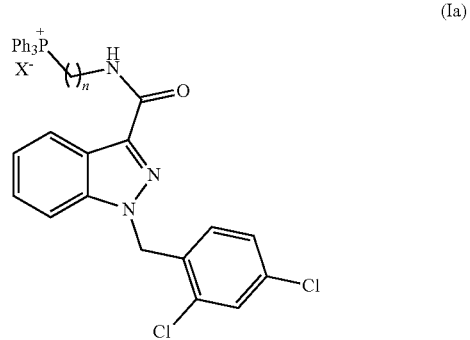

wherein n is an integer selected from 2 to 20, and wherein X is any halogen, 2,2,2-trifluoroacetic acid (TFA) or acetic acid. In one aspect, X is bromine. In yet another aspect, n is 10.

In some aspects, the present invention provides a composition comprising a mito-lonidamine compound described herein and a pharmaceutically acceptable carrier.

In yet another aspect, the invention provides a method of treating cancer in a subject in need thereof, the method comprising administering an effective amount of a mito-lonidamine compound of formula I:

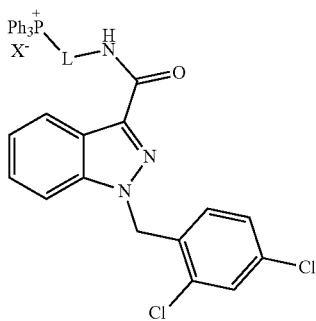

wherein L is a linker selected from an C2-C20 alkyl, an amino acid, benzyl, ramification of the alkyl side chain, a C2-C20 alkene or PEG, n is a positive integer selected from 2-20, and X is any halogen, 2,2,2-trifluoroacetic acid (TFA) or acetic acid. In some aspects, the method uses the mito-lonidamine compound is Mito-lonidamine of formula IIa:

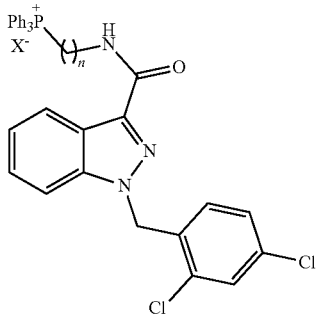

wherein n is selected from an integer of 2 to 20 and X is a halogen.

In another aspect, the invention provides a method of reducing cancer cell growth in a subject, the method comprising administering an effective amount of a mito-lonidamine compound of formula I:

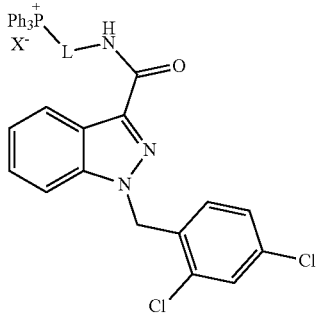

wherein L is a linker selected from an C2-C20 alkyl, an amino acid, benzyl, ramification of the alkyl side chain, a C2-C20 alkene or PEG, n is a positive integer selected from 2-20, and X is any halogen, 2,2,2-trifluoroacetic acid (TFA) or acetic acid.

In another aspect, the invention provides a method of reducing metastasis of a cancer in a subject, the method comprising administering an effective amount of a mito-lonidamine compound of formula I:

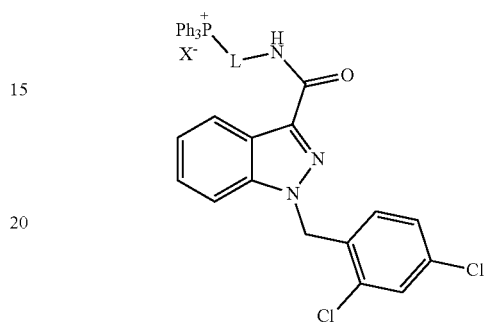

wherein L is a linker selected from an C2-C20 alkyl, an amino acid, benzyl, ramification of the alkyl side chain, a C2-C20 alkene or PEG, n is a positive integer selected from 2-20, and X is any halogen, 2,2,2-trifluoroacetic acid (TFA) or acetic acid.

The foregoing and other aspects and advantages of the invention will appear from the following description. In the description, reference is made to the accompanying drawings which form a part hereof, and in which there are shown, by way of illustration, preferred embodiments of the invention. Such embodiments do not necessarily represent the full scope of the invention, however, and reference is made therefore to the claims and herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 22A-22C depict the maximum tolerated dose (MTD) of mito-LON measured after 8-weeks treatment. (A) Measured body weight. (B) Serum levels of AST. (C) Serum levels of ALT.

DETAILED DESCRIPTION OF THE INVENTION

Figure 1A:
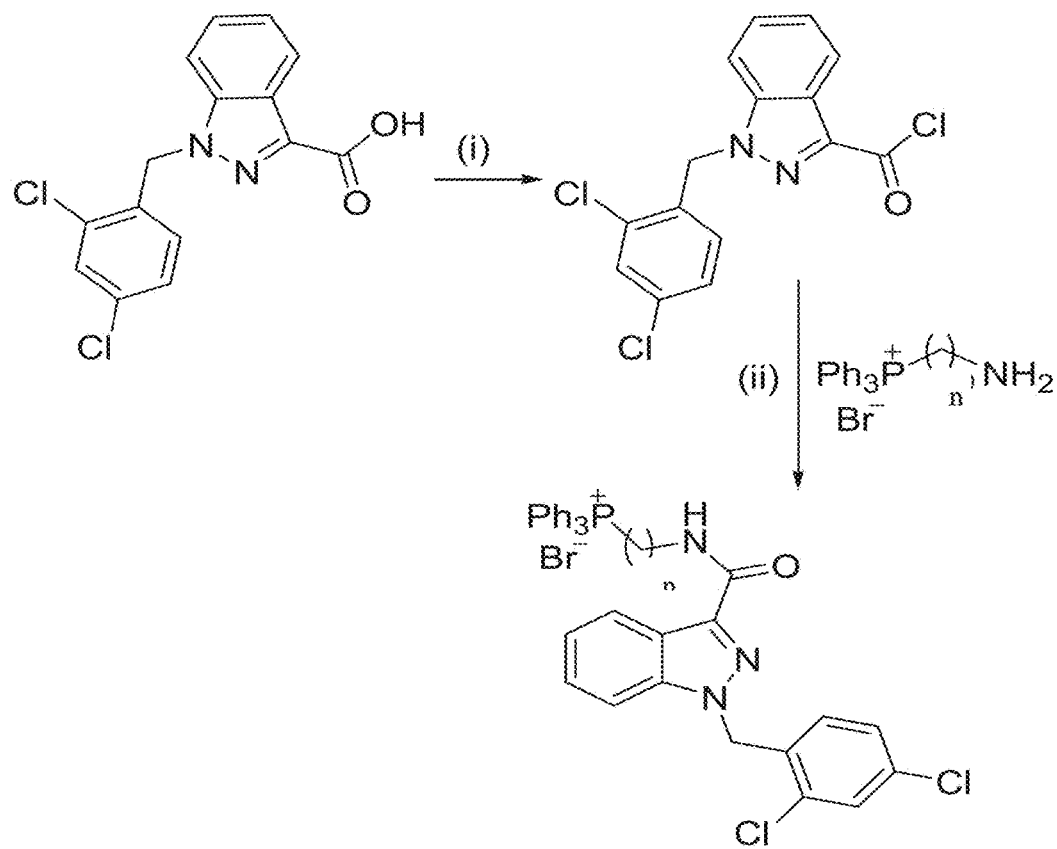
FIGS. 1A-1B show the schematic of synthesis of mito-lonidamine and mito$_{10}$-lonidamine respectively.

In General. Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

The abbreviations LON and LND are used interchangeably herein to refer to lonidamine. The abbreviations mito-LON and mito-LND are also used interchangeably and refer to the modified lonidamine of the present invention.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The Invention.

Compounds and Compositions. In one embodiment, the present invention provides novel mito-lonidamine (mito-LND or mito-LON) compounds modified to selectively and synergistically inhibit cancer proliferation and progression. Specifically, the inventors have shown that attaching a positively-charged group to lonidamine greatly enhances the compounds antitumor efficacy at very low doses when compared to lonidamine alone treatments.

In one embodiment, the mito-LND compounds of the present invention comprise lonidamine modified to include alkyl cationic moieties. Specifically, the lonidamine have been modified by the addition of a triphenylphosphonium cation (TPP+) via an alkyl chain. These modified mito-LND targets mitochondria and results in a significantly more potent form of LND for treatment of cancer and metastasis. The alkyl chain can comprise from 2 to 20 carbons in order to provide flexibility to not inhibit the function of LND.

As demonstrated in the Examples, Mito-lonidamine is significantly more potent (IC50=0.64 micromolar) than lonidamine (IC50=327 micromolar) in inhibiting the proliferation of cancer cells (human pancreatic cancer, lung cancer and brain metastasis) in vitro. Further, in vivo mouse models of non-small cell lung cancer demonstrate that mito-LDN is able to inhibit lung cancer cell growth and brain metastasis. Mito-lonidamine is>500-fold more potent than lonidamine in inhibiting mitochondrial Complex I activity of tumor cells than lonidamine. The inventors have surprisingly found that Mito-LDN not only could target the succinate-ubiquinone reductase activity of respiratory complex I and II but also that Mito-LDN is much more potent than LDN with $IC_{50}$ of 1.2 and 2.7 µM, respectively, in H2030BrM3 lung cancer cells (FIG. 9) demonstrating a greater than 100-fold potency as compared with LDN. Inhibition of complex I (and II) by Mito-LDN stimulates ROS generation (FIG. 12) and oxidizes mitochondrial Prx3 in lung cancer cells. These discoveries, for the first time, indicate that inhibiting mitochondrial complexes leading to autophagic cell death of preneoplastic and neoplastic cells is a key anti-tumor mechanism of Mito-LDN. This is surprising compared to LDN's effects on complex I and II, which occur at concentrations (ca. 400 µM, FIG. 7) that are well above the typical peak plasma levels (17-127 µM) in patients. The Example further demonstrates that Mito-LON is over 100-fold more effective than LON in inhibiting mitochondrial oxygen consumption (FIG. 9). Mito-LON is also>100-fold more potent than LON in inhibiting lung cancer proliferation and invasion.

The present invention provides mito-lonidamine and methods of use for treating cancer. In some embodiments, the mito-lonidamine may be administered alone or in combination with other chemotherapeutic agents, radiation, or other therapeutic modalities to treat various types of cancer, particularly high metabolic cancers. For example, in one embodiment, the mito-lonidamine may be used in treating cancer in combination with conventional chemotherapeutics, for example, but not limited to, paclitaxel, cis-platin, doxorubicin, gemcitabine, among others.

In one embodiment, the present invention provides a mito-lonidamine compound of formula I:

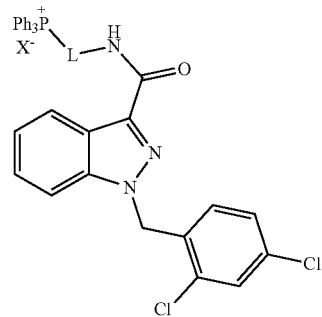

wherein L is a linker and n is selected from a positive integer from 2-20 and X is any halogen, 2,2,2-trifluoroacetic acid (TFA), or acetic acid.

Suitable linkers include an alkyl from 2 to 20 carbons, amino acids (e.g. arginine, lysine, etc), benzyl, ramificiation of the alkyl side chain, alkene (e.g. alkene with from 2 to 20 carbons), double bond, PEG, among others.

In a preferred embodiment, the mito-lonidamine compound of formula I comprises L of an alkyl wherein n is selected from 2 to 20, preferably in one embodiment where n is 10.

In one embodiment, X is a halogen, and the halogen is selected from the group consisting of bromine (Br), fluorine (F), chlorine (Cl), iodine (I) and astatine (At). In a preferred embodiment, the halogen is bromine.

In another embodiment, present invention provides a mito-lonidamine compound of formula I wherein L is an alkyl, n is selected from a positive integer from 2-20 as depicted in the following Formula Ia:

(Ia)

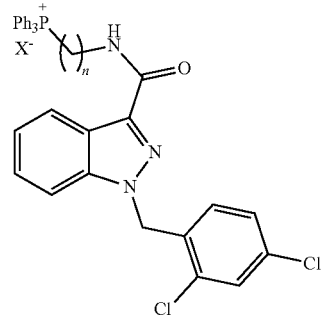

In a preferred embodiment, the mito-lonidamine compound of formula Ia comprises X is bromide and n is a positive integer from 5-20, alternatively n is a positive integer from 10-20. In a preferred embodiment, n is 10.

In another embodiment, the present invention provides a mito-lonidamine compound of formula I, wherein L is an alkyl and X is bromide as depicted in formula (Ib):

(Ib)

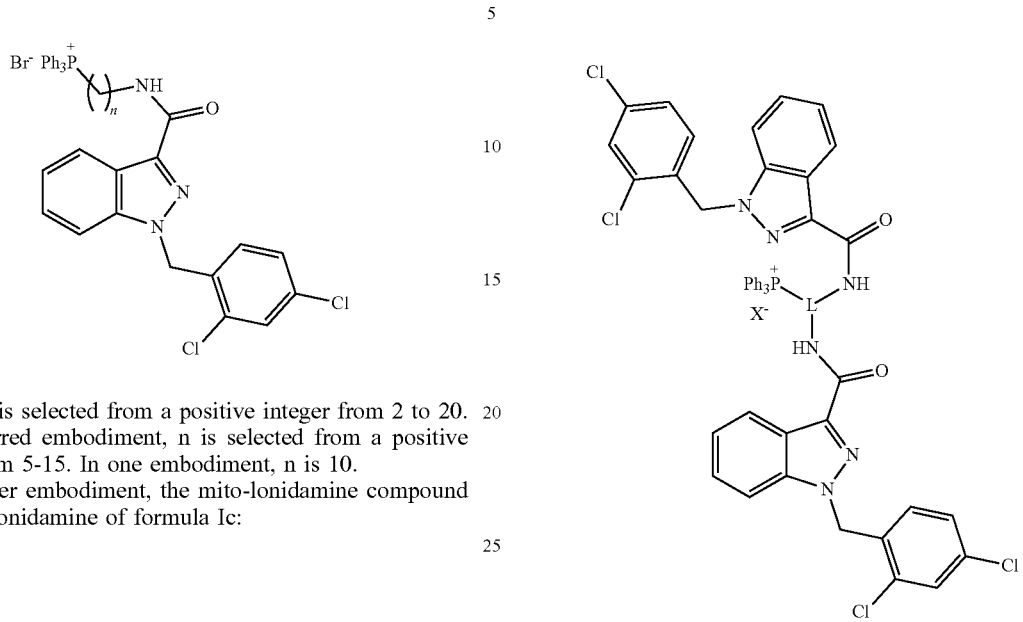

wherein n is selected from a positive integer from 2 to 20. In a preferred embodiment, n is selected from a positive integer from 5-15. In one embodiment, n is 10.

In another embodiment, the mito-lonidamine compound is Mito$_{10}$-lonidamine of formula Ic:

(Ic)

In another embodiment, the mit-lonidamine compound is formula II:

wherein L is a linker, n is selected from a positive integer from 2-20 and X is any halogen, 2,2,2-trifluoroacetic acid (TFA), or acetic acid. In one embodiment, X is a halogen, and the halogen is selected from the group consisting of bromine (Br), fluorine (F), chlorine (Cl), iodine (I) and astatine (At). In a preferred embodiment, the halogen is bromine.

Suitable linkers (L) include an alkyl from 2 to 20 carbons, benzyl, ramificiation of the alkyl side chain, amino acids, double bond, alkene (e.g. alkene with from 2 to 20 carbons), PEG, among others.

In alternate embodiments, the invention comprises a mito-LND compound according to the following structure

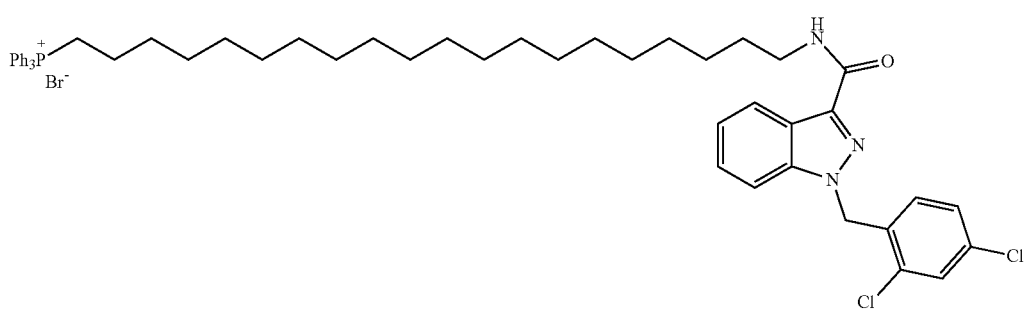

Mito$_{20}$-LND

In alternate embodiments, the invention comprises a mito-LND compound according to the following structure

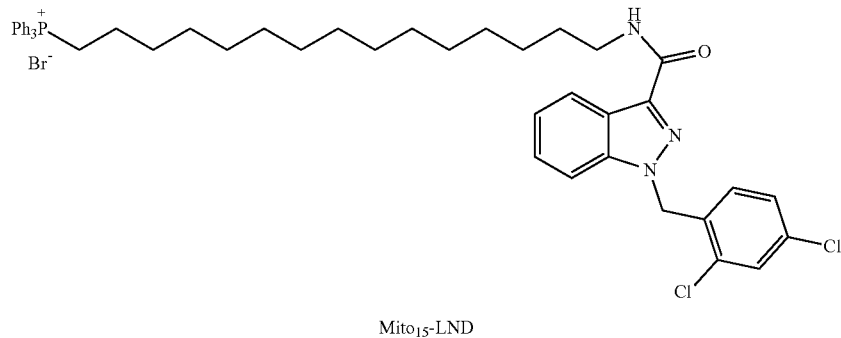

Mito₁₅-LND

In alternate embodiments, the invention comprises a mito-LND compound according to the following structure

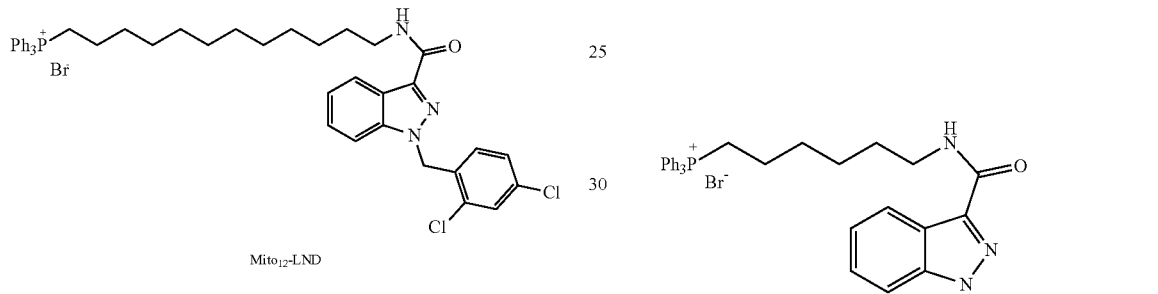

Mito₁₂-LND

In alternate embodiments, the invention comprises a mito-LND compound according to the following structure

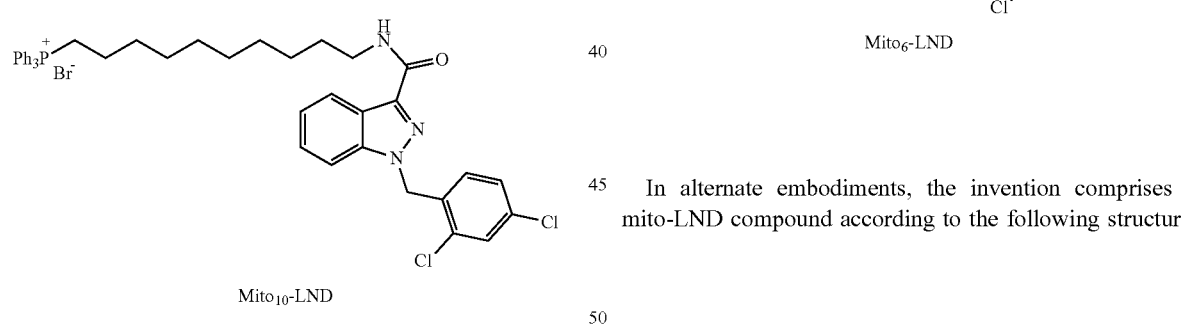

Mito₁₀-LND

In alternate embodiments, the invention comprises a mito-LND compound according to the following structure

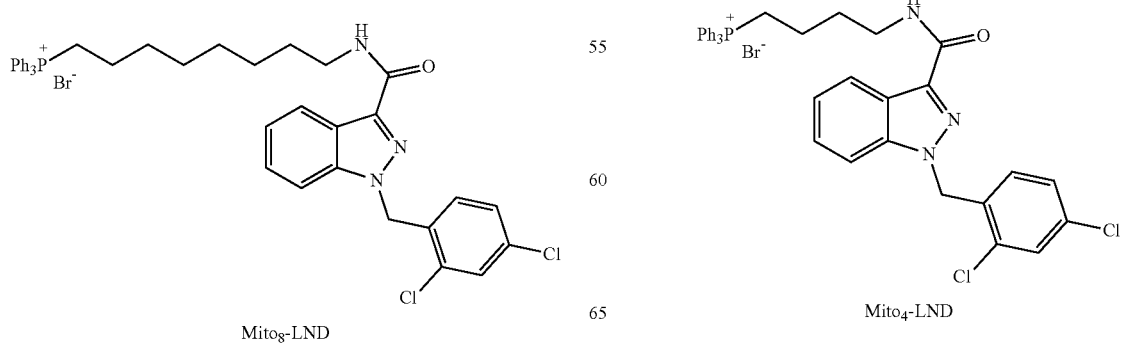

Mito₈-LND

In alternate embodiments, the invention comprises a mito-LND compound according to the following structure Mito₆-LND In alternate embodiments, the invention comprises a mito-LND compound according to the following structure Mito₄-LND In alternate embodiments, the invention comprises a mito-LND compound according to the following structure

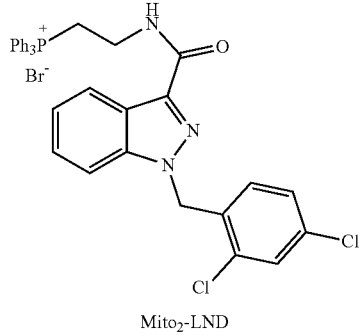

Mito₂-LND

In alternate embodiments, the invention comprises a mito-LND compound according to the following structure

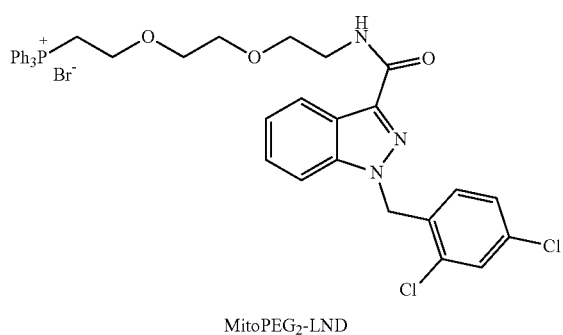

MitoPEG₂-LND

In alternate embodiments, the invention comprises a mito-LND compound according to the following structure

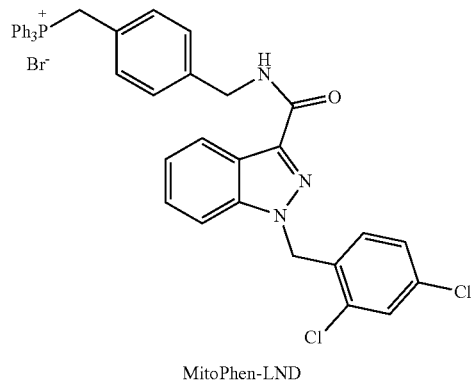

MitoPhen-LND

In alternate embodiments, the invention comprises a mito-LND compound according to the following structure

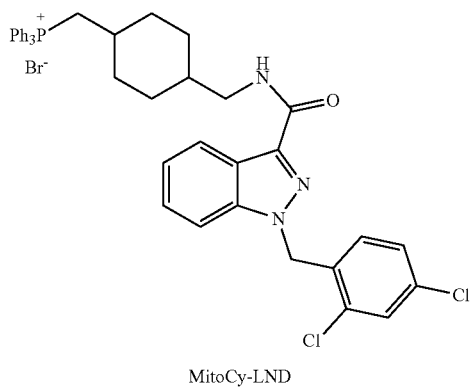

MitoCy-LND

In alternate embodiments, the invention comprises a mito-LND compound according to the following structure (isomers of Mito12-LND)

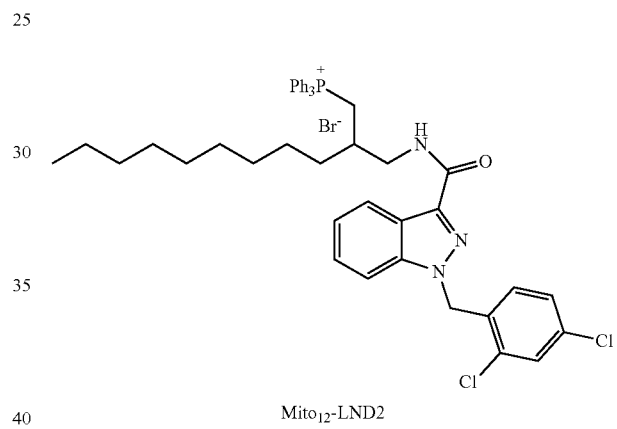

Mito₁₂-LND2

In alternate embodiments, the invention comprises a mito-LND compound according to the following structure (isomers of Mito10-LND)

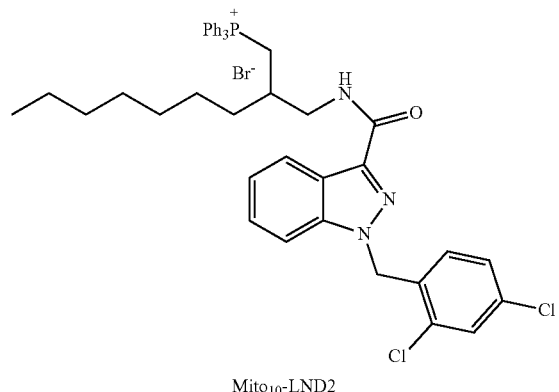

Mito₁₀-LND2

In alternate embodiments, the invention comprises a mito-LND compound according to the following structure (isomers of Mito₉-LND)

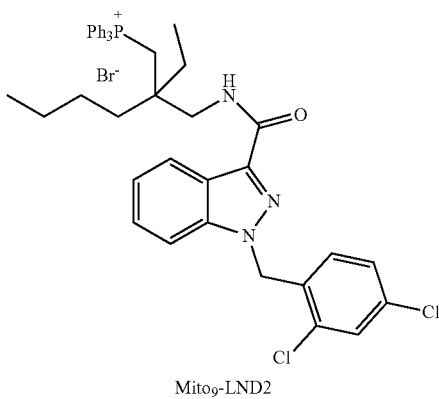

Mito₉-LND2

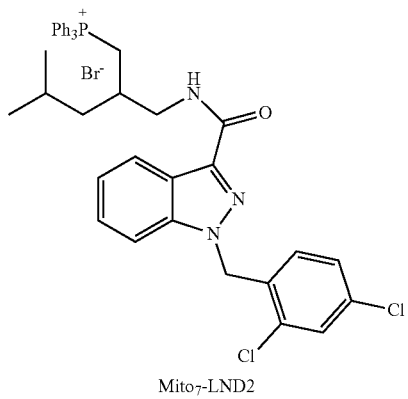

Mito₇-LND2

In alternate embodiments, the invention comprises a mito-LND compound according to the following structure (isomers of Mito₈-LND)

In alternate embodiments, the invention comprises a mito-LND compound according to the following structure (isomers of Mito₆-LND)

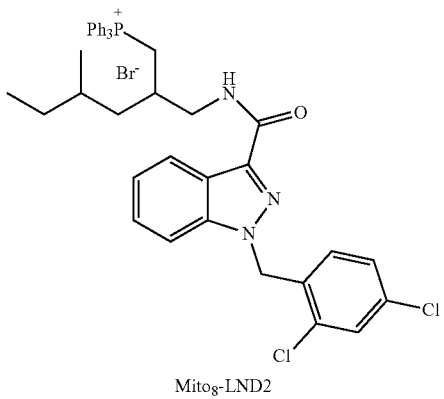

Mito₈-LND2

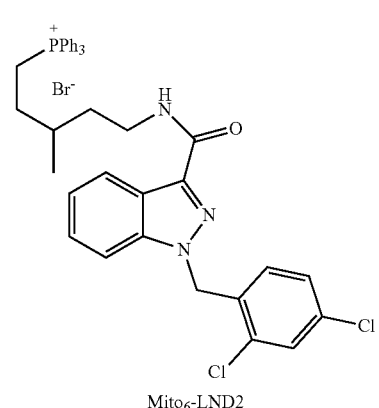

Mito₆-LND2

In alternate embodiments, the invention comprises a mito-LND compound according to the following structure (isomers of Mito₇-LND)

In alternate embodiments, the invention comprises a mito-LND compound according to the following structure

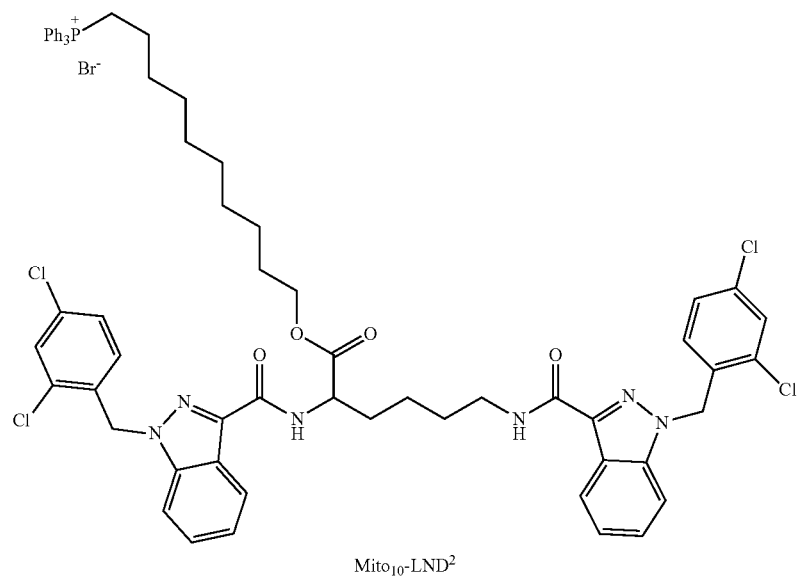

Mito₁₀-LND²

In some embodiments, the disclosure provides compositions comprising at least one mito-lonidamine compound of the present invention. The compositions may further include a pharmaceutically acceptable carrier. In a preferred embodiment, the mito-lonidamine compound is mito$_{10}$-lonidamine of formula II.

"Pharmaceutically acceptable" carriers are known in the art and include, but are not limited to, for example, suitable diluents, preservatives, solubilizers, emulsifiers, liposomes, nanoparticles and adjuvants. Pharmaceutically acceptable carriers are well known to those skilled in the art and include, but are not limited to, 0.01 to 0.1 M and preferably 0.05M phosphate buffer or 0.9% saline. Additionally, such pharmaceutically acceptable carriers may be aqueous or non-aqueous solutions, suspensions, and emulsions. Examples of nonaqueous solvents are propylene glycol, polyethylene glycol, vegetable oils such as olive oil, and injectable organic esters such as ethyl oleate. Aqueous carriers include isotonic solutions, alcoholic/aqueous solutions, emulsions or suspensions, including saline and buffered media.

Pharmaceutical compositions of the present disclosure may include liquids or lyophilized or otherwise dried formulations and may include diluents of various buffer content (e.g., Tris-HCl, acetate, phosphate), pH and ionic strength, additives such as albumin or gelatin to prevent absorption to surfaces, detergents (e. g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, milamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

In some embodiments, the compositions comprise a pharmaceutically acceptable carrier, for example, buffered saline, and the like. The compositions can be sterilized by conventional, well known sterilization techniques. The compositions may contain pharmaceutically acceptable additional substances as required to approximate physiological conditions such as a pH adjusting and buffering agent, toxicity adjusting agents, such as, sodium acetate, sodium chloride, potassium chloride, calcium chloride, sodium lactate, and the like.

Methods of Synthesis: The mito-lonidamine compounds using a alkyl linker of the present invention are prepared by the two-step process depicted in FIG. 1 or as described below. A solution of lonidamine, oxalyl chloride and a catalytic amount of DMF in $CH_2Cl_2$ is heated under reflux. Unreacted oxalyl chloride and solvent were removed under reduced pressure to yield 1-(2,4-dichlorobenzyl)-1H-indazole-3-carbonyl chloride. The 1-(2,4-dichlorobenzyl)-1H-indazole-3-carbonyl chloride was subsequently reacted with the corresponding aminoalkyltriphenylphosphonium bromide at room temperature to produce the Mito-lonidamine (Mito-LDN). The Mito-LDN is purified either by flash chromatography or on HPLC.

Methods of Use: In one embodiment, the invention provides a method of treating cancer in a subject comprising administering to the subject a therapeutically effective amount of a composition comprising at least one mito-lonidamine compound of the present invention. In one embodiment, the composition comprises one mito-lonidamine compound of the present invention. In a preferred embodiment, the mito-lonidamine compound is mito$_{10}$-lonidamine compound of formula II. In another embodiment, the compositions comprises two or more mito-lonidamine compounds of the present invention.

For purposes of the present invention, "treating" or "treatment" describes the management and care of a subject for the purpose of combating the disease, condition, or disorder. Treating includes the administration of an inhibitor of present invention to prevent the onset of the symptoms or complications, alleviating the symptoms or complications, or eliminating the disease, condition, or disorder. Treating also encompasses therapeutic and palliative treatment. The aim of treatment includes the alleviation or prevention of symptoms, slowing or stopping the progression or worsening of a disease, disorder, or condition and/or the remission of the disease, disorder or condition. In certain embodiments, the treatment comprises anti-cancer therapy and/or treatments. The term "treatment" can be characterized by at least one of the following: (a) the reducing, slowing or inhibiting the growth of cancer and cancer cells, including slowing or inhibiting the growth of metastatic cancer cells; (b) preventing the further growth of tumors; (c) reducing or preventing the metastasis of cancer cells within a subject; (d) reducing or ameliorating at least one symptom of cancer. In some embodiments, the optimum effective amount can be readily determined by one skilled in the art using routine experimentation.

The term "effective amount" or "therapeutically effective amount" refers to an amount sufficient to effect beneficial or desirable biological and/or clinical results. That result can be reducing, inhibiting or preventing the growth of cancer cells, reducing, inhibiting or preventing metastasis of the cancer cells or invasiveness of the cancer cells or metastasis, or reducing, alleviating, inhibiting or preventing at least one symptoms of the cancer or metastasis thereof, or any other desired alteration of a biological system. An "effective treatment" refers to treatment producing a beneficial effect, e.g., amelioration of at least one symptom of a cancer. A beneficial effect can take the form of an improvement over baseline, i.e., an improvement over a measurement or observation made prior to initiation of therapy according to the method. A beneficial effect can also take the form of reducing, inhibiting or preventing further growth of cancer cells, reducing, inhibiting or preventing metastasis of the cancer cells or invasiveness of the cancer cells or metastasis or reducing, alleviating, inhibiting or preventing at least one symptoms of the cancer or metastasis thereof. Such effective treatment may, e.g., reduce patient pain, reduce the size or number of cancer cells, may reduce or prevent metastasis of a cancer cell, or may slow cancer or metastatic cell growth.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, intraaural administration, intracerebral administration, rectal administration, sublingual administration, buccal administration, and parenteral administration, including injectable such as intravenous administration, intra-arterial administration, intramuscular administration, intradermal administration, intrathecal administration and subcutaneous administration. Administration can be continuous or intermittent. In various aspects, a preparation can be administered therapeutically; that is, administered to treat an existing disease or condition. In a preferred embodiment, the compounds or compositions are administered by intravenous, oral or inhalation.

For oral administration, the active ingredient may be combined with at least one solid inactive ingredient for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents, or lubricating agents.

As is known in the art, a cancer is generally considered as uncontrolled cell growth. The methods of the present invention can be used to treat any cancer, any metastases thereof, and any chemo-residual growth thereof, including, but not limited to, carcinoma, lymphoma, blastoma, sarcoma, and leukemia. Suitable cancers able to be treated by the compositions, methods and kits described herein include, but are not limited to, breast cancer, prostate cancer, colon cancer, squamous cell cancer, small-cell lung cancer, non-small cell lung cancer, ovarian cancer, cervical cancer, gastrointestinal cancer, pancreatic cancer, glioblastoma, liver cancer, bladder cancer, hepatoma, colorectal cancer, uterine cervical cancer, endometrial carcinoma, salivary gland carcinoma, mesothelioma, kidney cancer, vulval cancer, pancreatic cancer, thyroid cancer, hepatic carcinoma, skin cancer, melanoma, brain cancer, neuroblastoma, myeloma, various types of head and neck cancer, acute lymphoblastic leukemia, acute myeloid leukemia, Ewing sarcoma, and peripheral neuroepithelioma. In one embodiment, the cancer is selected from melanoma, non-small cell lung cancer, squamous cell carcinoma of the head and neck, ovarian cancer, pancreatic cancer, renal cell carcinoma, hepatocellular carcinoma, bladder cancer, malignant glioma, colorectal cancer, and endometrial cancer.

In some embodiments, the cancer is a pancreatic cancer, non-small cell lung cancer or brain cancer. In one embodiment, the cancer is pancreatic cancer. In another embodiment, the cancer is non-small cell lung cancer (NSCLC). In a further embodiment, the cancer is brain metastasis from NSCLC.

In one embodiment, the cancer is brain cancer. It is believed that mito-lonidamine is able to cross the blood brain barrier and thus provides a treatment of brain cancer. In some embodiments, the at least one mito-lonidamine compound is combined with standard cancer therapy, for example radiation, to treat brain cancer.

The terms "metastasis" or "secondary tumor" refer to cancer cells that have spread to a secondary site, e.g., outside of the original primary cancer site. Secondary sites include, but are not limited to, for example, the lymphatic system, skin, distant organs (e.g., liver, stomach, pancreas, brain, etc.), and the like, and will differ depending on the site of the primary tumor.

In one embodiment, the present compounds and compositions are used to treat metastasis of cancer, specifically brain metastasis.

The present disclosure also provides methods of reducing cancer cell growth, the method comprising contacting or administering the cancer cell with a therapeutically effective amount of at least one mito-lonidamine compound of formula I to reduce the cancer cell growth.

In another embodiment, the disclosure provides a method of reducing or inhibiting metastasis of a cancer in a subject, the method comprising administering an effective amount of the mito-lonidamine compound or compositions described herein.

In some embodiments, the at least one mito-lonidamine compound is used in combination with radiation or chemotherapy. Suitable chemotherapeutic agents are known in the art and may vary depending on the type of cancer to be treated. Suitable chemotherapeutic agents include, but are not limited to, for example, paclitaxel, cis-platin, doxorubicin, gemcitabine, among others.

As used herein "subject" or "patient" refers to mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex. In one specific embodiment, a subject is a mammal, preferably a human.

In some embodiments, kits for carrying out the methods described herein are provided. The kits provided may contain the necessary components with which to carry out one or more of the above-noted methods. In one embodiment, a kit for treating cancer is provided. The kit may comprise at least one mito-lonidamine compound of the present invention and instructions for use. In some embodiments, the kit may further comprise one or more conventional cancer treatments to use in combination with the at least one mito-lonidamine compound. In one embodiment, the kit comprises $mito_{10}$-lonidamine.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. The term "consisting essentially of" and "consisting of" should be interpreted in line with the MPEP and relevant Federal Circuit's interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim.

The present invention has been described in terms of one or more preferred embodiments, and it should be appreciated that many equivalents, alternatives, variations, and modifications, aside from those expressly stated, are possible and within the scope of the invention.

The invention will be more fully understood upon consideration of the following non-limiting examples.

EXAMPLES

Figure 1B:
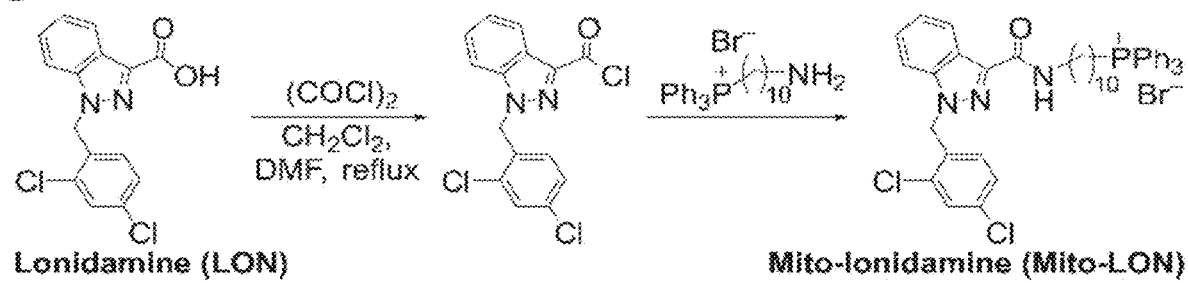

Example 1: Making of Mito-Lonidamine and Mitochondria-Targeting of Mito-Lonidamine FIG. 1A shows a general schematic of making of Mito-lonidamine. FIG. 1B shows the specific making of $Mito_{10}$-

Lonidamine. All chemicals and organic solvents were commercially available and were used as supplied. The reactions were monitored by TLC using silica gel Merck [60]F254. Crude materials were purified by flash chromatography on Merck Silica gel 60 (0.040-0.063 mm). $^1$H NMR spectra were recorded at 400.13 MHz respectively using a Bruker DPX AVANCE 400 spectrometer equipped with a QNP probe. $^1$H NMR and $^{31}$P were taken in $CDCl_3$ using $CDCl_3$ and TMS as internal reference respectively. Chemical shifts (δ) are reported in ppm and J values in Hertz.

The synthesis of Mito-Lonidamine is shown in FIGS. 1A and 1B. A solution of 1-(2,4-dichlorobenzyl)-1H-indazole-3-carboxylic acid (0.35 g, 1.1 mmol), oxalyl chloride (2 mL) and a catalytic amount of DMF (0.1 mL) in $CH_2Cl_2$ (20 mL) was heated under reflux for 2 h. Unreacted oxalyl chloride and solvent were removed under reduced pressure to yield 1-(2,4-dichlorobenzyl)-1H-indazole-3-carbonyl chloride as a yellow solid. (10-aminodecyl) triphenylphosphonium bromide (0.54 g, 1.1 mmol) and triethylamine (160 µL, 1.1 mmol) were added to a solution of the acid chloride in $CH_2Cl_2$ (20 mL) and the reaction mixture was stirred for 12 h at room temperature and then washed with water (30 mL). The organic layer was dried over $Na_2SO_4$ and the solvent distilled under reduced pressure. Purification of the crude product by flash chromatography on a silicagel ($CH_2Cl_2$/EtOH 90:10) afforded a yellow powder (0.4 g, 46%), corresponding to $Mito_{10}$-lonidamine ($Mito_{10}$-LDN).

Figure 3:
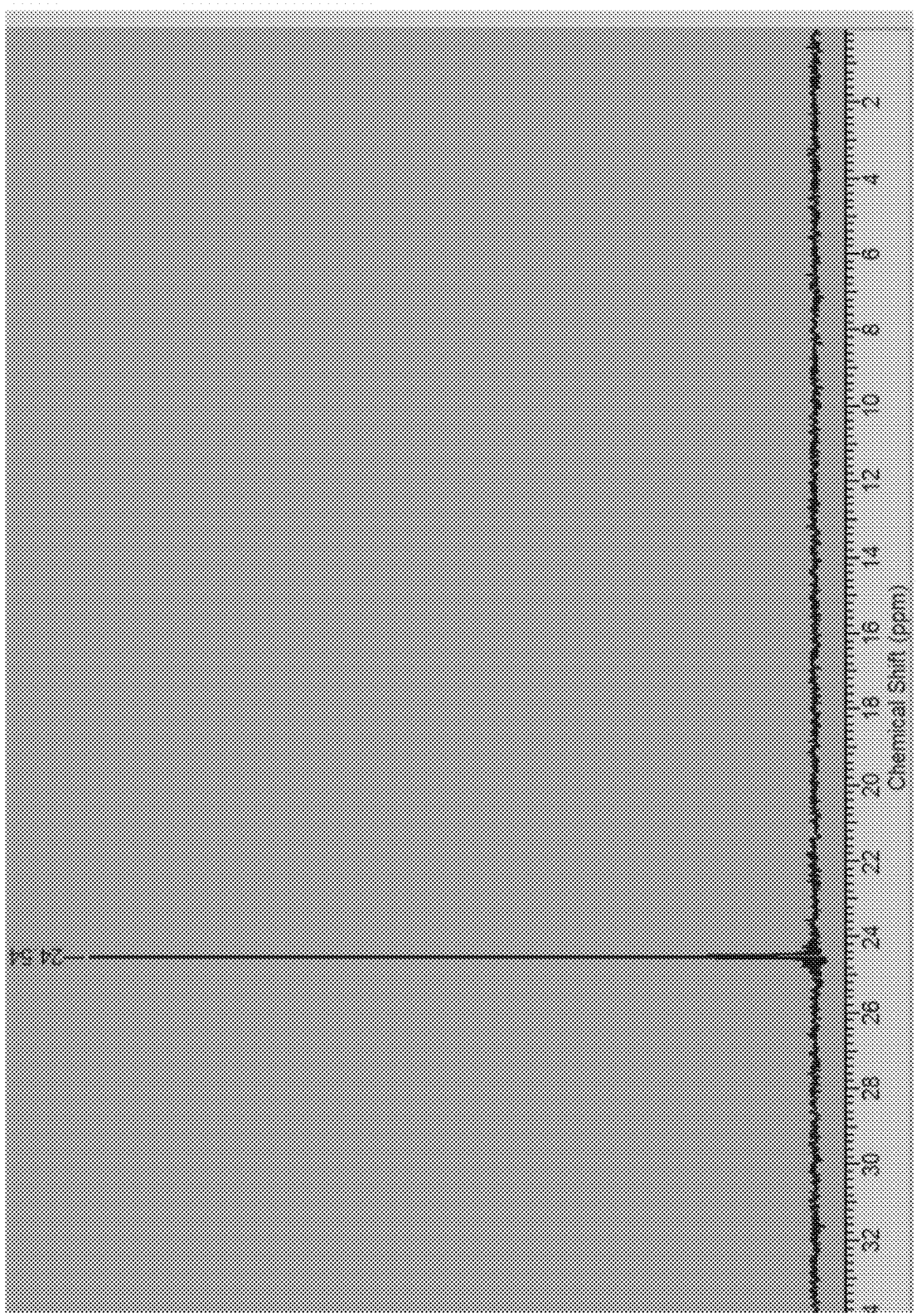
FIG. 3 is the $^{31}$P NMR spectrum of mito-lonidamine (400.13 MHz, CDCl$_3$).
Figure 4:
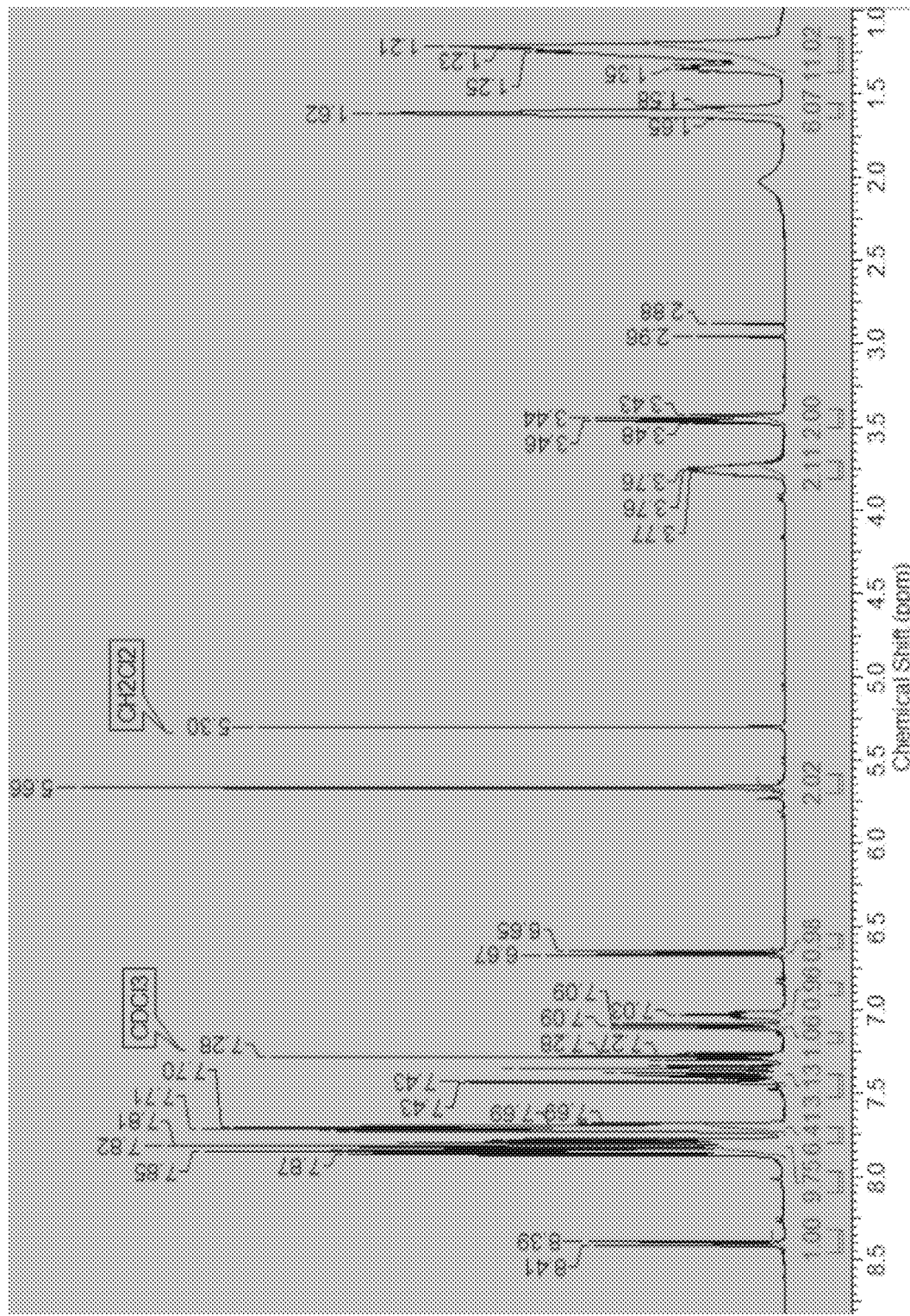
FIG. 4 is the $^1$H NMR spectrum of mito-lonidamine (400.13 MHz, CDCl$_3$).
Figure 5:
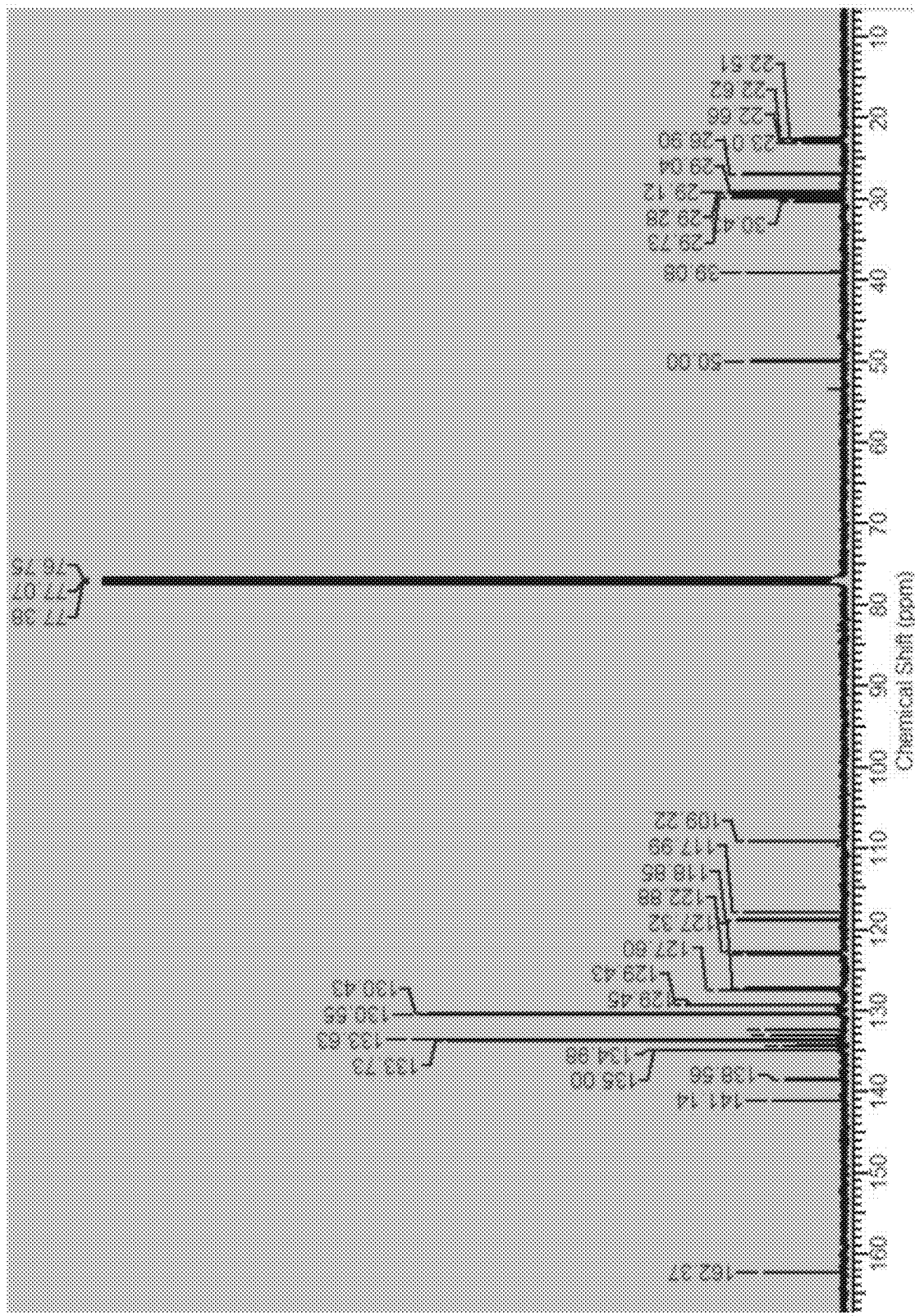
FIG. 5 is the $^{13}$C NMR spectrum of mito-lonidamine (75 MHz, CDCl$_3$).

Linking the LDN molecule to $TPP^+$ via a long alkyl chain increases its lipophilicity and enhances cellular uptake. The long alkyl chain separating the $TPP^+$ group from LON minimizes the effect of $TPP^+$ on LDN's pharmacophore activity. $Mito_{10}$-LDN was synthesized from LON as shown in FIG. 1B, and characterized by NMR and mass spectrometry (FIGS. 3-5). $TPP^+$-linked compounds accumulate selectively and to high levels in cancer cell mitochondria,[53] according to the Nernst equation (FIG. 10), consistent with the pronounced effects of Mito-LON on complex I and II at low µM concentrations (FIG. 9).

HRMS calculated for $Mito_{10}$-lonidamine $C_{43}H_{45}Cl_2N_3OP$ $[M]^+$ 720.2672, found, 720.2672.

Figure 2:
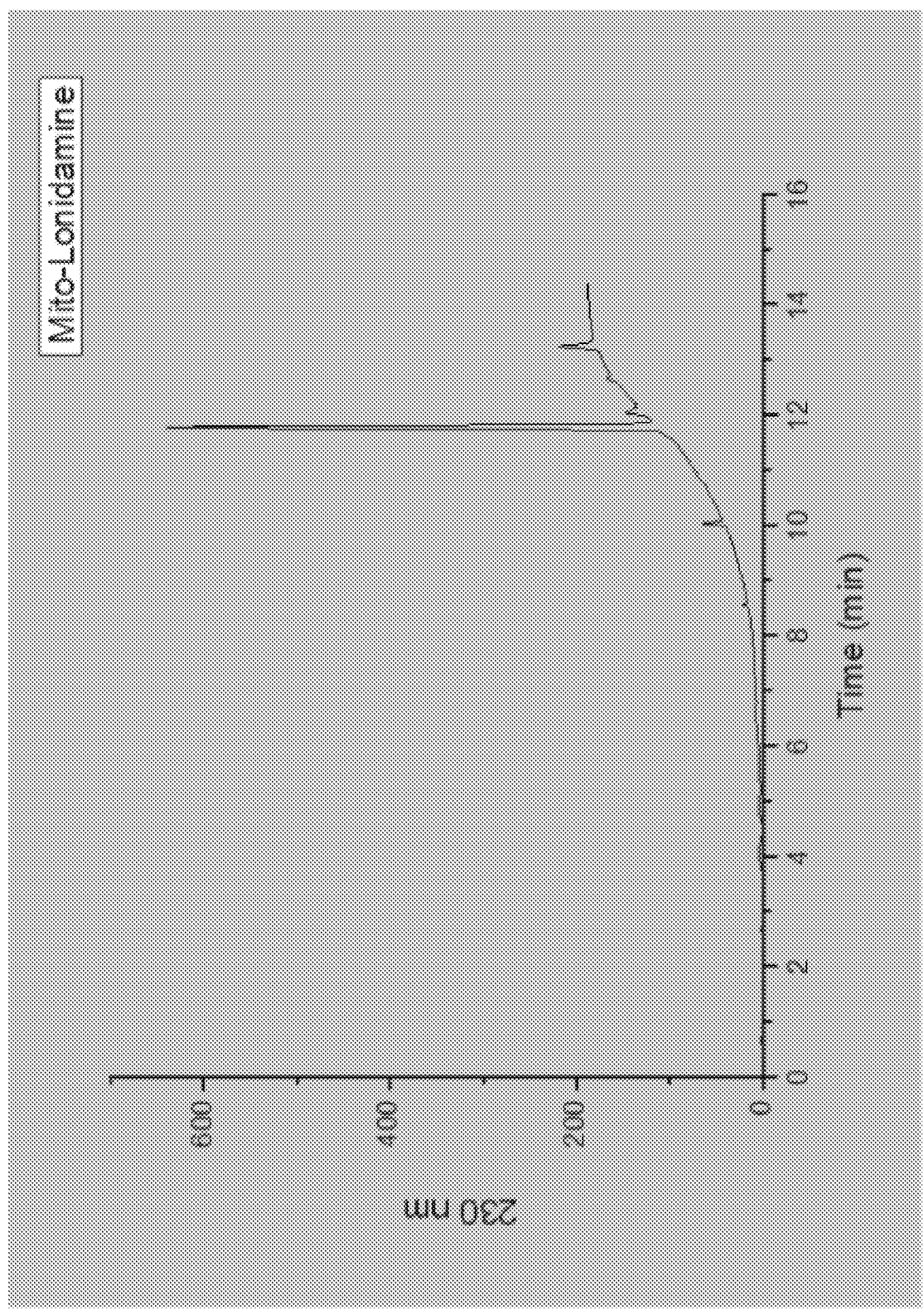
FIG. 2 is a HPLC trace for mito-lonidamine.

$^{31}$P (400.13 MHz, $CDCl_3$) δ 24.38, 24.54. $^1$H NMR (400.13 MHz, $CDCl_3$) δ 8.40 (1H, d, J=8.1), 7.88-7.78 (9H, m), 7.74-7.69 (6H, m), 7.43 (1H, d, J=2.2), 7.42-7.33 (2H, m), 7.30-7.26 (1H, m), 7.1 (1H, dd, J=2.0, 8.3), 7.03 (1H, bt, J=5.9), 6.66 (1H, d, J=8.3), 5.66 (2H, s), 3.78-3.71 (2H, m), 3.45 (2H, dt, J=6.8, 7.1), 1.70-1.56 (6H, m), 1.31-1.17 (10H, m). $^{13}$C NMR (75.47 MHz, $CDCl_3$) δ 162.4, 141.1, 138.6, 135.0, 134.9, 134.4, 133.7, 133.6, 133.1, 132.4, 130.5, 130.4, 129.4, 129.4, 127.6, 127.3, 123.1, 123.0, 122.8, 118.8, 117.9, 109.2, 50.0, 39.0, 30.4, 30.3, 29.7, 29.3, 29.2, 29.1, 29.0, 26.9, 23.0, 22.7, 22.6, 22.5. HPLC trace is shown in FIG. 2.

Using the same procedure, Mito-Lonidamines containing various alkyl linker side chain (n=2-20) or using other linkers (e.g. benzyl, ramificiation of the alkyl side chain, double bound, PEG, amino acids, etc.) can be synthesized. Specifically, the various alkly linker side chain are synthesized as depicted (FIG. 1A). $^1$H NMR and $^{31}$P were taken in $CDCl_3$ using $CDCL_3$ and TMS as internal reference respectively, as shown in FIGS. 3-5.

The $mito_n$-lonidamine compounds of the present invention are synthesized according to the following reaction:

Scheme.

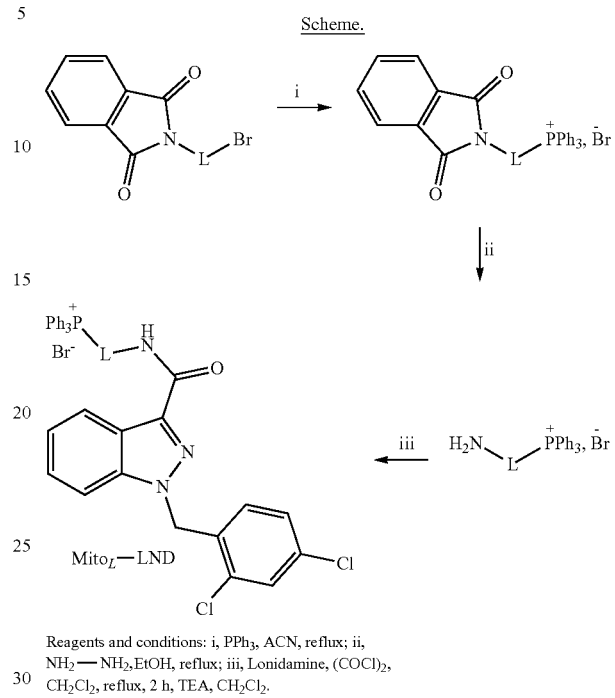

Reagents and conditions: i, $PPh_3$, ACN, reflux; ii, $NH_2$—$NH_2$,EtOH, reflux; iii, Lonidamine, $(COCl)_2$, $CH_2Cl_2$, reflux, 2 h, TEA, $CH_2Cl_2$.

In a specific embodiment, the reaction is:

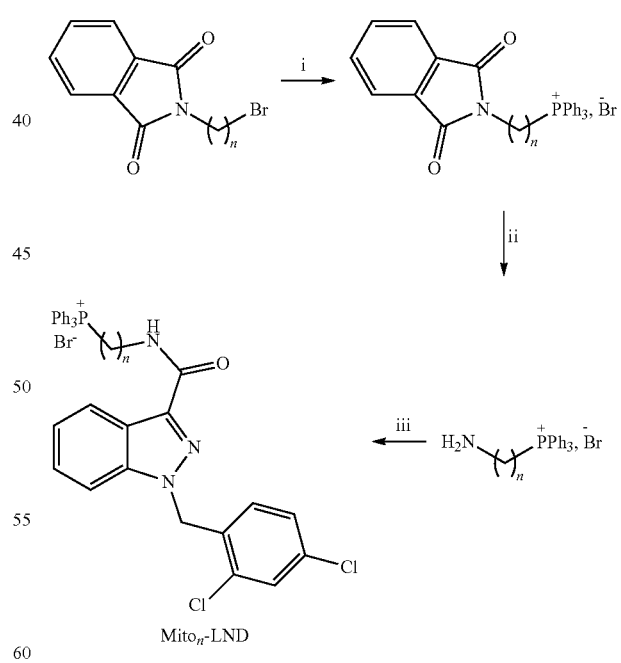

wherein i, $PPh_3$, ACN, reflux; ii, $NH_2$-$NH_2$, EtOH, reflux; iii, Lonidamine, $(COCl)_2$, $CH_2Cl_2$, reflux, 2 h, TEA, $CH_2Cl_2$.

The Mito-PEG-LND compounds of the present invention are synthesized according to the following reaction:

Scheme.
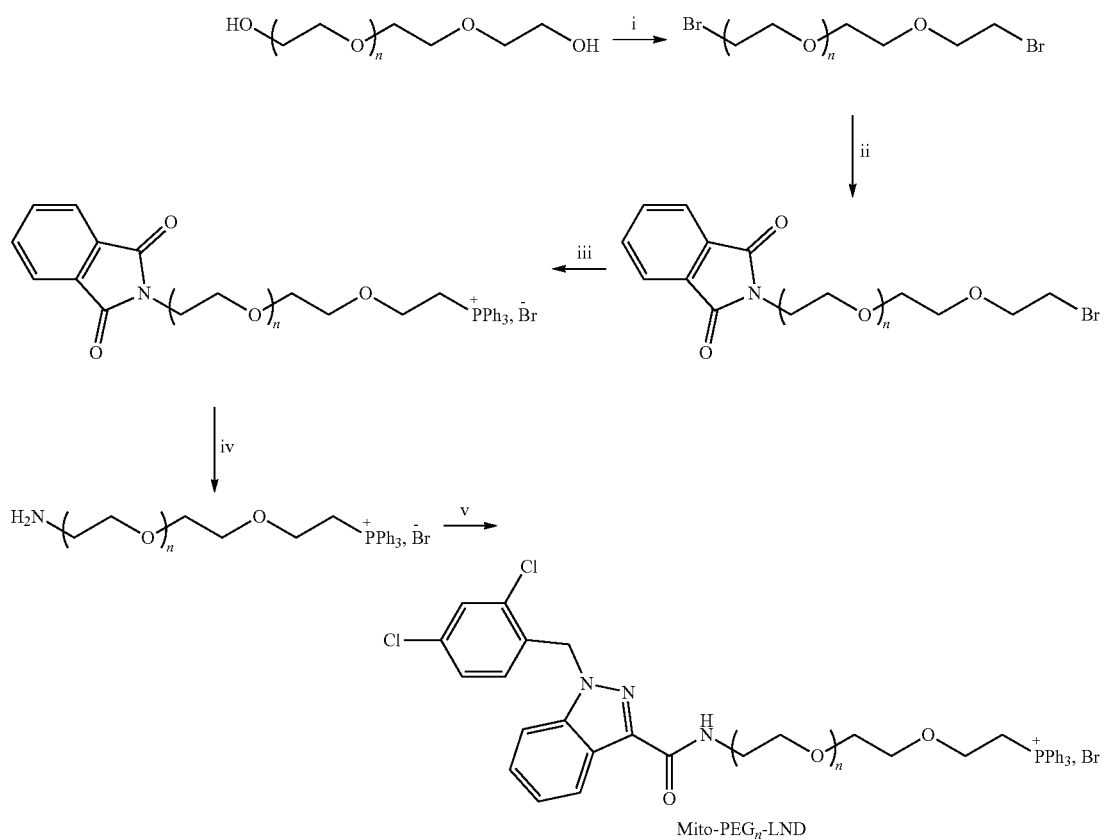
Reagents and conditions: i, PBr$_3$; ii, Potassium phtalimide, DMF; iii, PPh$_3$, ACN, reflux; iv, NH$_2$—NH$_2$, reflux; v, Lonidamine, (COCl)$_2$, CH$_2$Cl$_2$, reflux, 2 h, TEA, CH$_2$Cl$_2$.
In some embodiments, n is an integer selected from 1 to 10.
The Mito-Phen-LND compounds of the present invention are synthesized according to the following reaction:
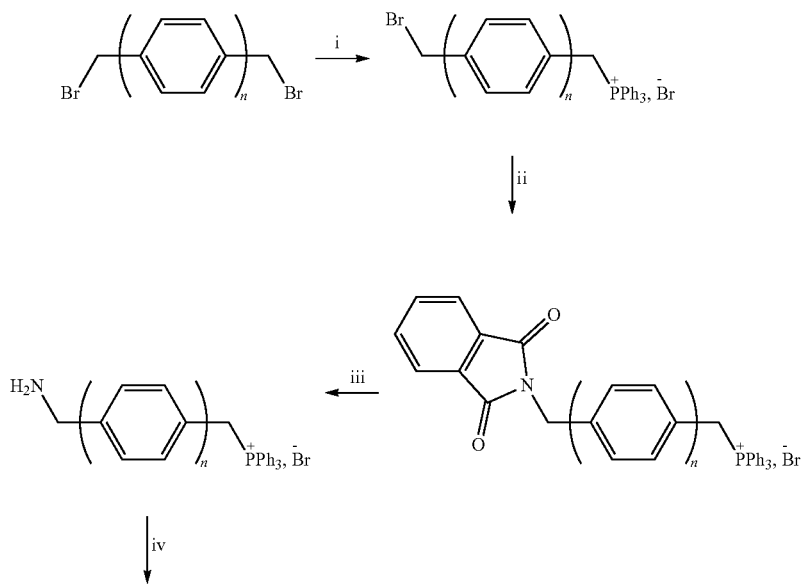

-continued

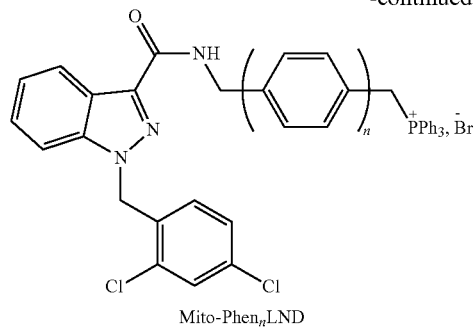

Mito-Phen$_n$LND

Reagents and conditions: i, PPh$_3$, ACN, reflux; ii, Potassium phtalimide, DMF; iii, NH$_2$-NH$_2$, EtOH, reflux; iv, Lonidamine, (COCl)$_2$, CH$_2$Cl$_2$, reflux, 2 h, TEA, CH$_2$Cl$_2$.

In some embodiments, n is an integer selected from 1 to 10.

The Mito-Cy-LND compounds of the present invention are synthesized according to the following reaction:

Mito-LND are attributed to the unexpected change in the mechanism of inhibition of mitochondrial energy metabolism.

Relative Anti-Proliferative Effects of LND and Mito-LND in Tumor Cells.

Pancreatic cancer cells were treated with either LND or Mito-LND at varying concentrations and the number of cells Scheme.

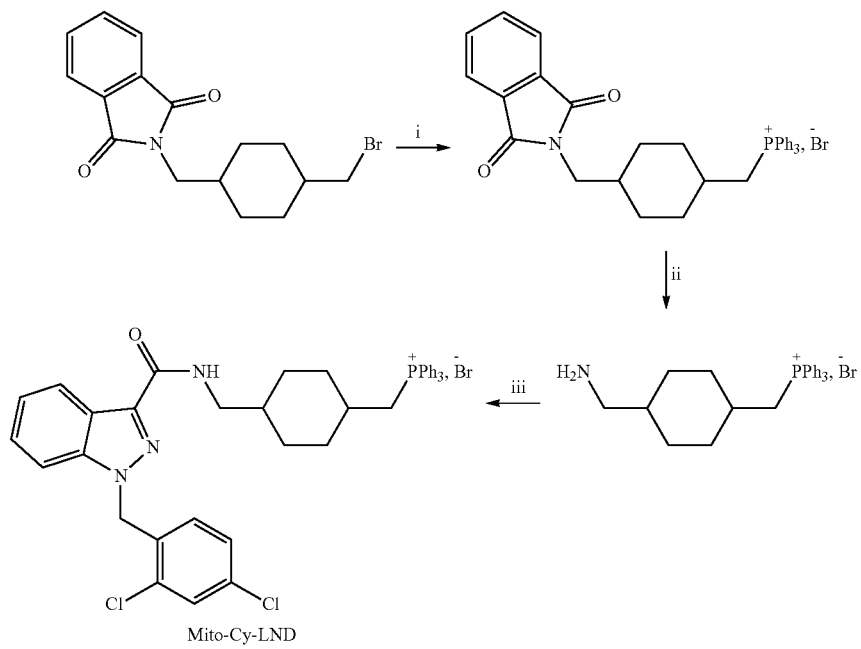

Mito-Cy-LND

Reagents and conditions: i, PPh$_3$, ACN, reflux; ii, NH$_2$—NH$_2$, EtOH, reflux; iii, Lonidamine, (COCl)$_2$, CH$_2$Cl$_2$, reflux, 2 h, TEA, CH$_2$Cl$_2$

Example 2: Anti-Tumor Effects of Mito-Lonidamine in Pancreatic Cancer

Figures 6A, 6B, 6C:
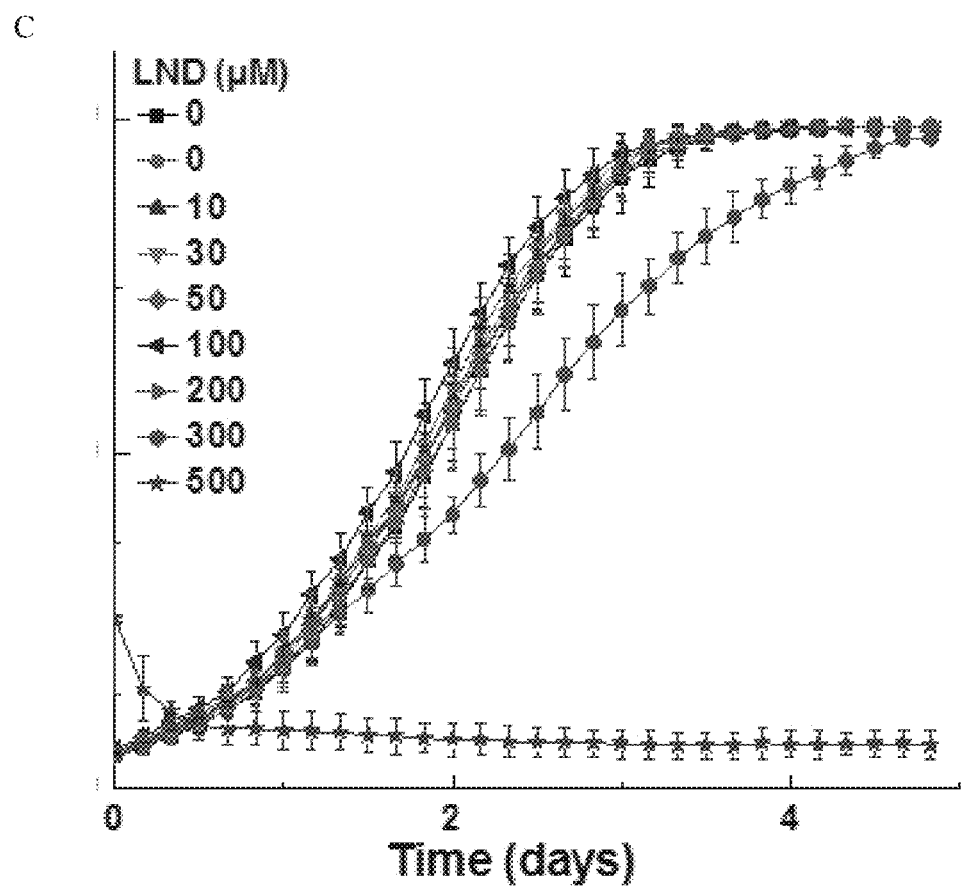
FIGS. 6A-6C demonstrates the relative anti-proliferative effects of LND and mito-LND in pancreatic tumor cells.

The present Example shows the modification of the structure of lonidamine such that the modified compound exhibits antitumor effects similar or exceeding those of LND incorporated to nanoparticles. Modified LND (mito-lonidamine (MLND or Mito-LND)) is mechanistically very different from LND. The increased antitumor effects of was assayed over time. As demonstrated in FIG. 6, Mito-LND was nearly 500-fold more effective in its anti-proliferative effects of pancreatic cancer cells.

Figure 7:
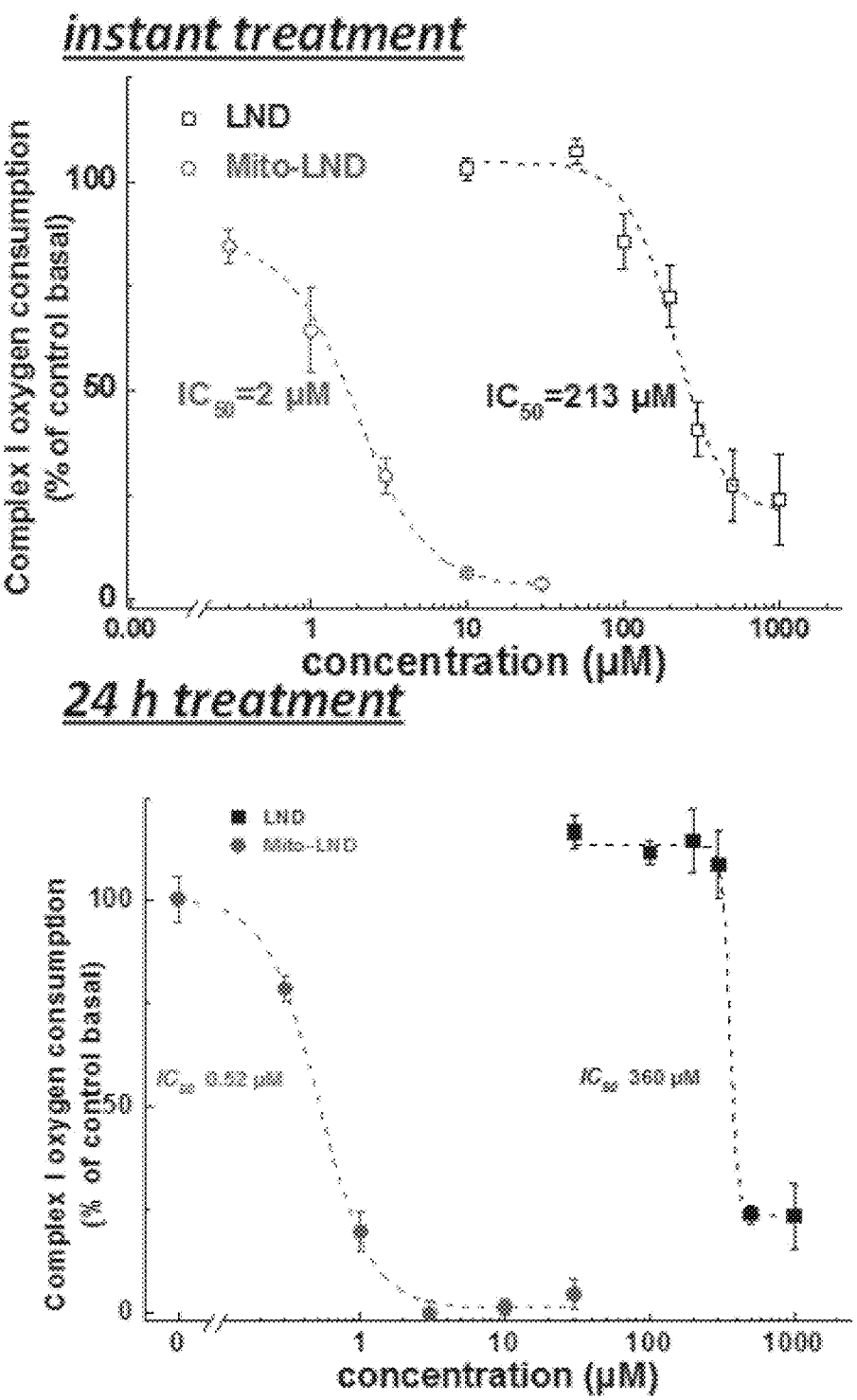
FIG. 7 demonstrates the relative inhibition of mitochondrial Complex I by lonidamine and mito-LND in pancreatic cancer cells.
Figure 7:
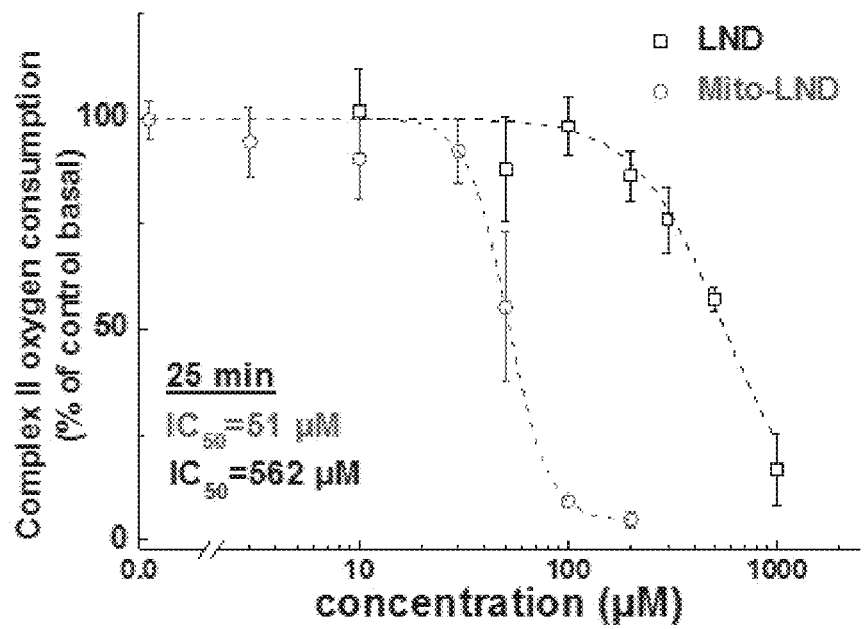
Figure 7:
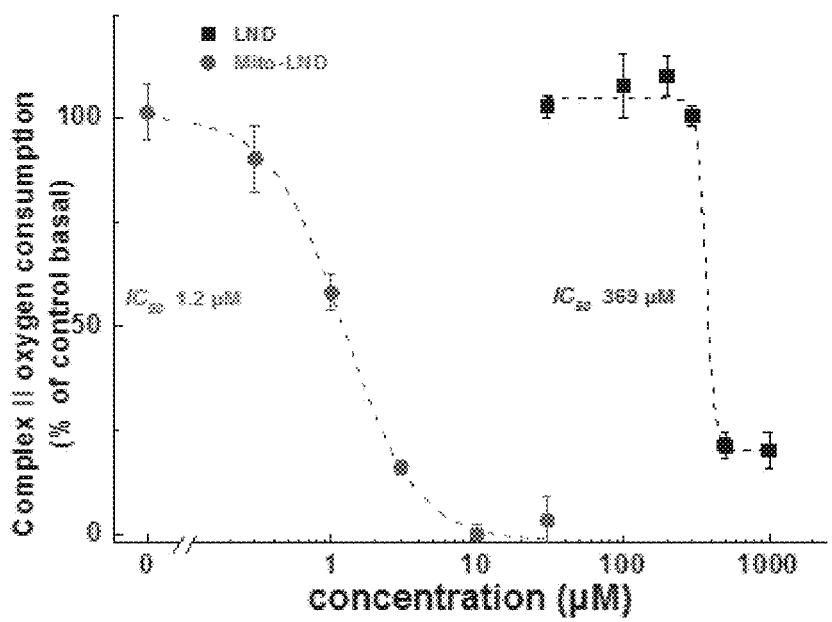
Figure 8:
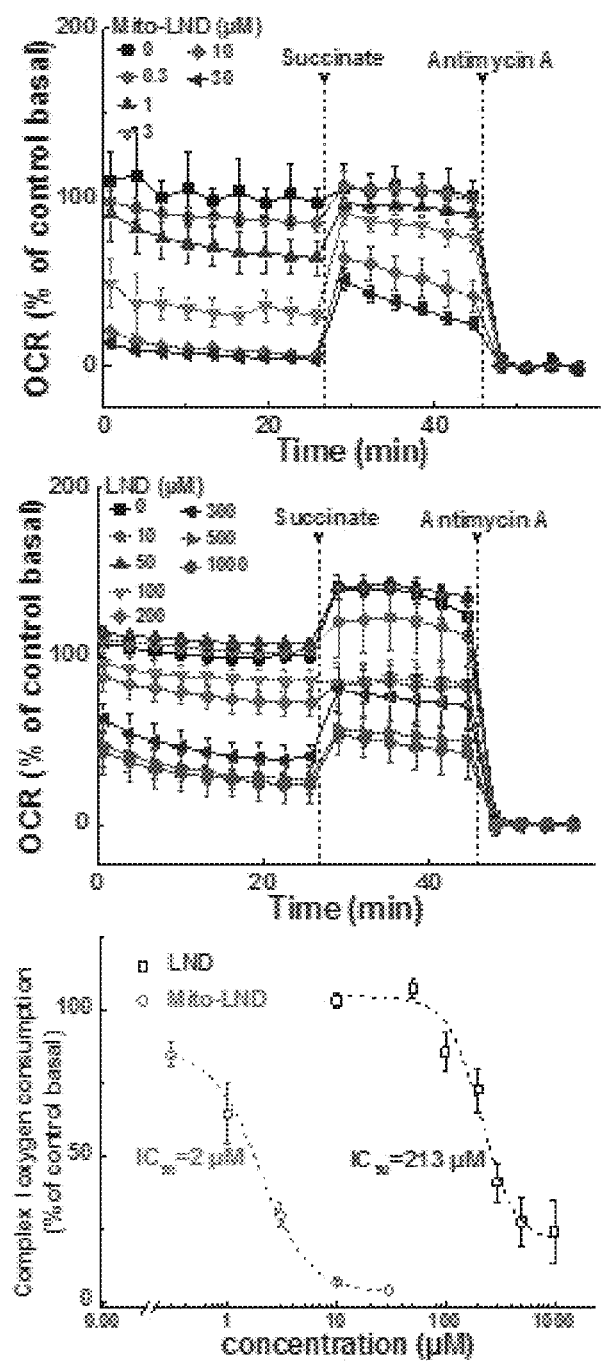
FIG. 8 shows the effects of lonidamine and mito-lonidamine on mitochondrial respiration monitored using the Seahorse analyzer.
Figure 8:
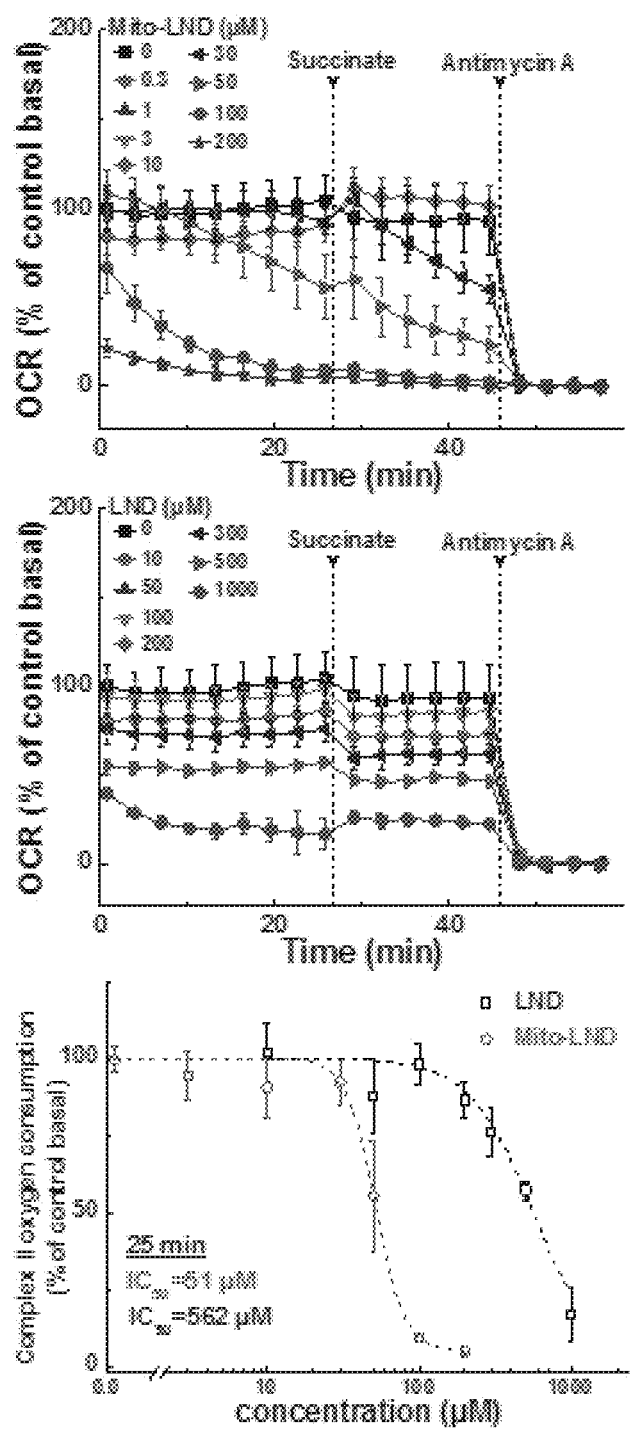
Figure 8:
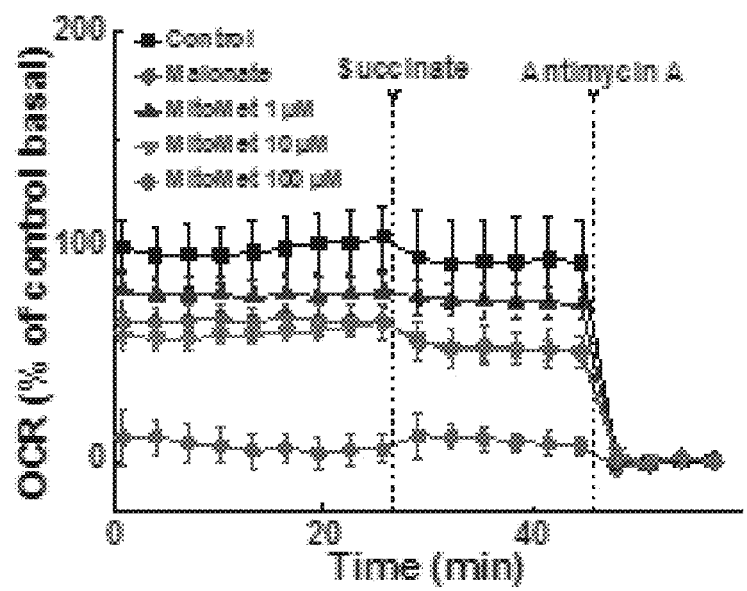
Figure 8:
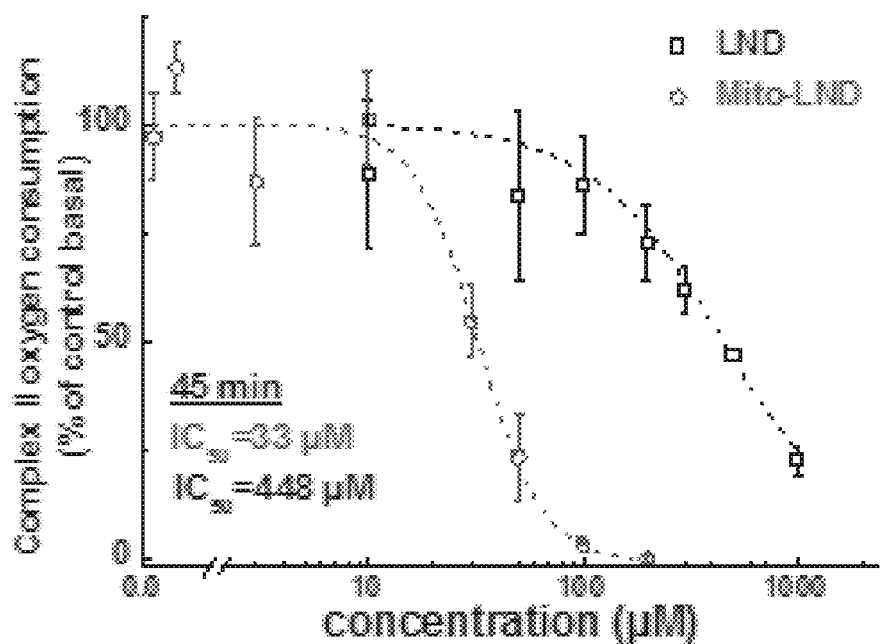

To investigate the mechanism of mitochondrial inhibition, we measured the activity of mitochondrial complexes in tumor cells. The cell membrane was permeabilized, and OCR was measured upon addition of substrates and inhibitors of mitochondrial complexes I-II. Surprisingly, as shown in FIG. 7, Mito-LND inhibits Complex I more potently than Complex II and that Mito-LND is >500-fold more potent than LND in inhibiting the Complex I activity of tumor cells (FIGS. 7 and 8).

Example 3: Anti-Proliferative Effects of Mito-LND in Lung Cancer Model

Non-small cell lung cancers (NSCLCs) are the most common lung cancers[9] and ~40% of NSCLCs are adenocarcinomas (LUAD). Current and former smokers have increased LUAD risk. Brain metastases are one of the most intractable clinical problems associated with LUAD and one of the leading causes of LUAD mortality[6,10]. The only available therapies for central nervous system (CNS) metastases are whole brain/CNS irradiation or surgical resection, or treatment with anti-EGFR agents in patients with EGFR mutations[6]. These therapies are purely palliative and have significant toxicity.

This example demonstrates that Mito-LND is able to reduce lung tumorigenesis and associated brain metastasis in a mouse model using Mito$_{10}$-Lonidamine.

The inventors have surprisingly found that Mito-LON not only could target the succinate-ubiquinone reductase activity of respiratory complex I and II but also that Mito-LON is much more potent than LON with $IC_{50}$ of 1.2 and 2.7 µM, respectively, in H2030BrM3 lung cancer cells (FIG. 9). Inhibition of complex I (and II) by Mito-LON stimulates ROS generation (FIG. 12) and oxidizes mitochondrial Prx3 in lung cancer cells. These discoveries, for the first time, indicate that inhibiting mitochondrial complexes leading to autophagic cell death of preneoplastic and neoplastic cells is a key anti-tumor mechanism of Mito-LON. This is surprising compared to LON's effects on complex I and II, occur at concentrations (ca. 400 µM, FIG. 2) that are well above the typical peak plasma levels (17-127 µM) in patients.[19,20]

In vitro studies have shown LON, by itself, to be only moderately effective at clinically relevant concentrations (<130 µM).[3] While LON can also inhibit mitochondrial complex II,[3, 17] this occurs at levels well above those achieved clinically.

Figure 12A:
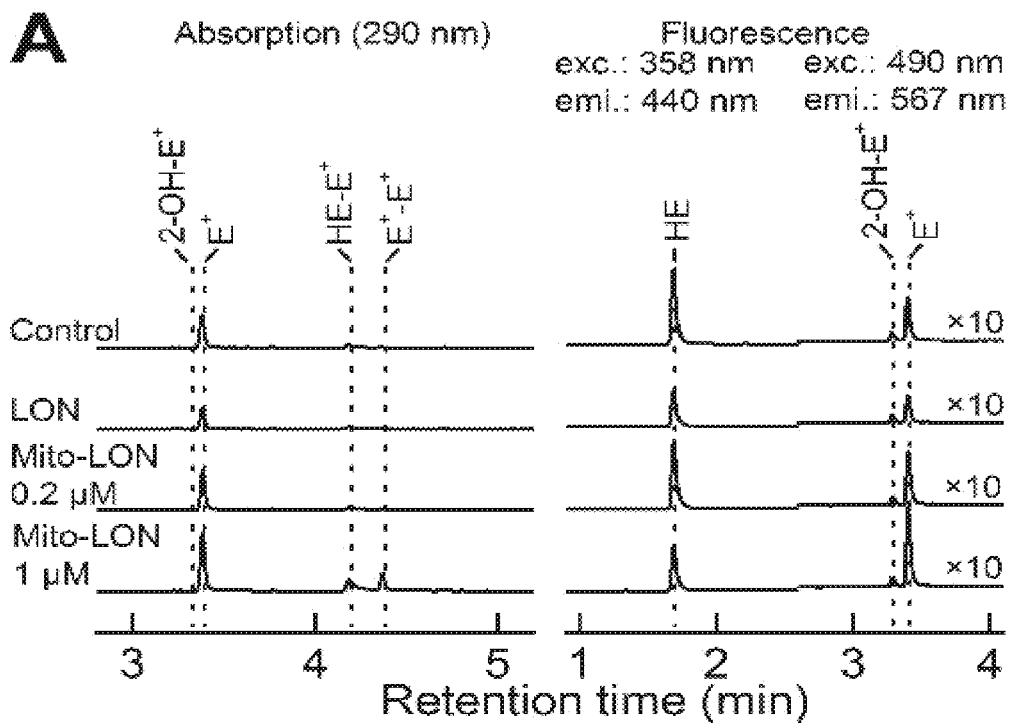
FIGS. 12A-12B depict the effect of LON and Mito-LON on cellular ROS production, as measured by HPLC-based analyses of oxidation of hydroethidine (HE) probe. (A) HPLC traces recorded; (B) quantitative data. $*p<0.05$.
Figure 12B:
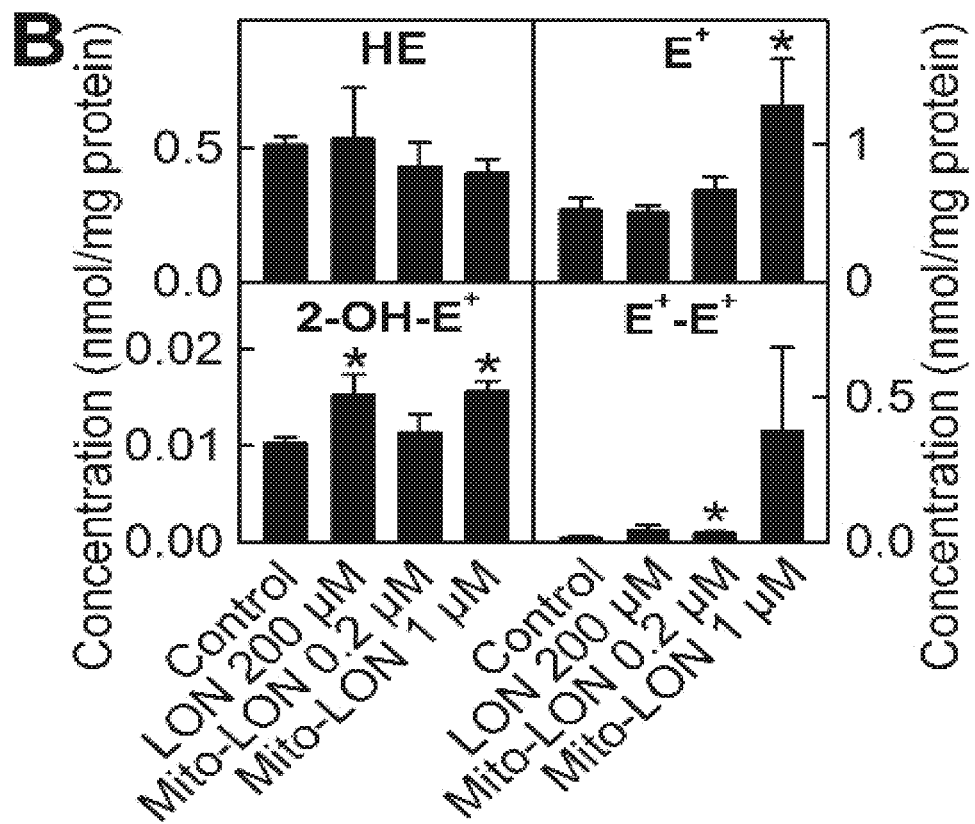
Figure 13:
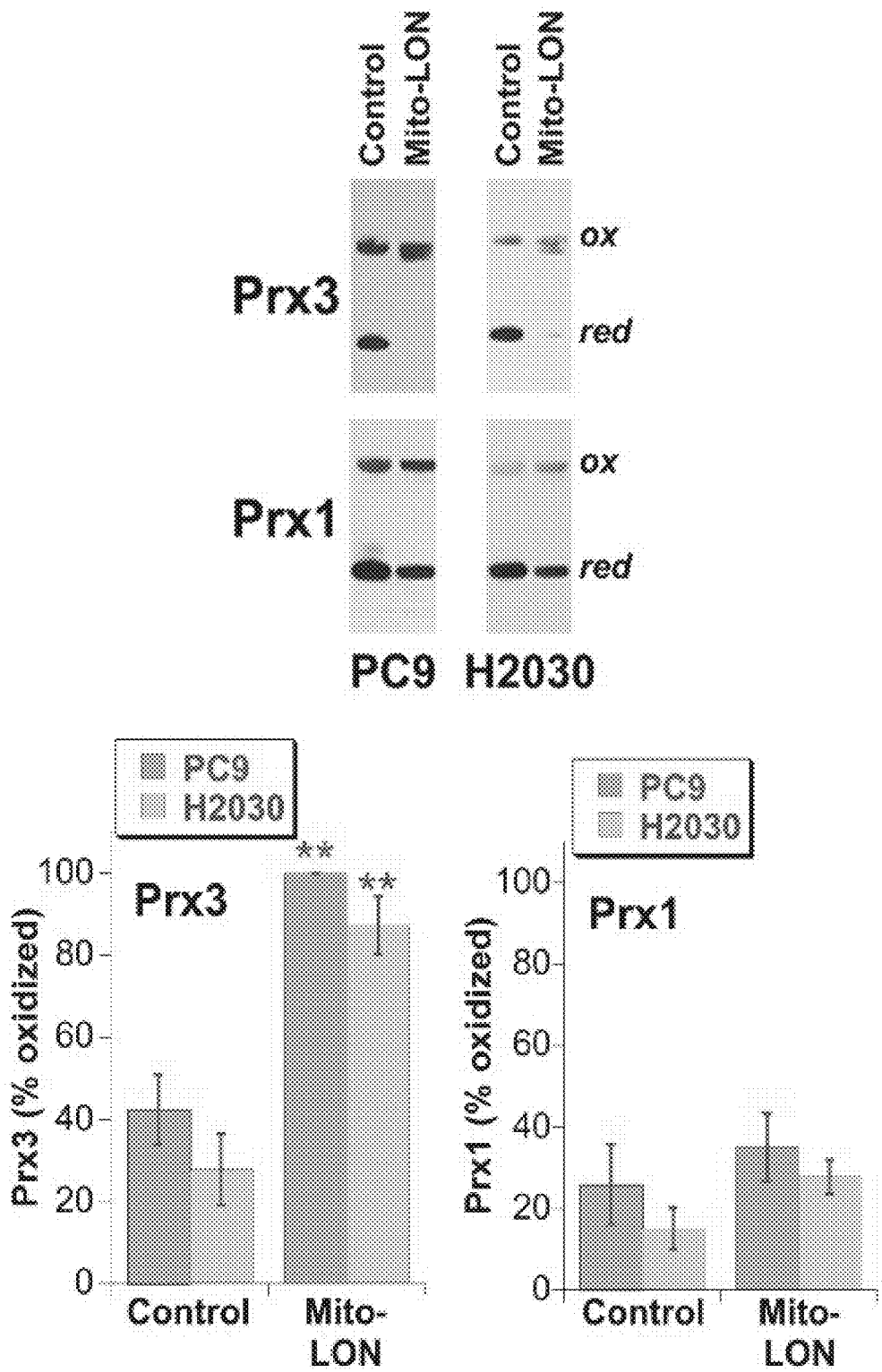
FIG. 13 depicts the effect of LON and Mito-LON on redox status of cytosolic (Prx1) and mitochondrial (Prx3) peroxiredoxins. $**p<0.01$.

This Example shows that Mito-LON is over 100-fold more effective than LON in inhibiting mitochondrial oxygen consumption (FIG. 9). Mechanistically, Mito-LON is >100-fold more potent than LON and it inhibits complex I ($K_i$=1.2 µM) more so than complex II ($K_i$=2.7 µM) (FIG. 9). Mito-LON is also >100-fold more potent than LON in inhibiting lung cancer proliferation and invasion. Pretreatment of H2030BrM3 cells with LON ($IC_{50}$~400 µM) or Mito-LON ($IC_{50}$~2 µM) caused inhibition of complex I and II (FIG. 2B). Further Mito-LON induced ROS generation in mitochondria (FIGS. 12 and 13).

Figure 11:
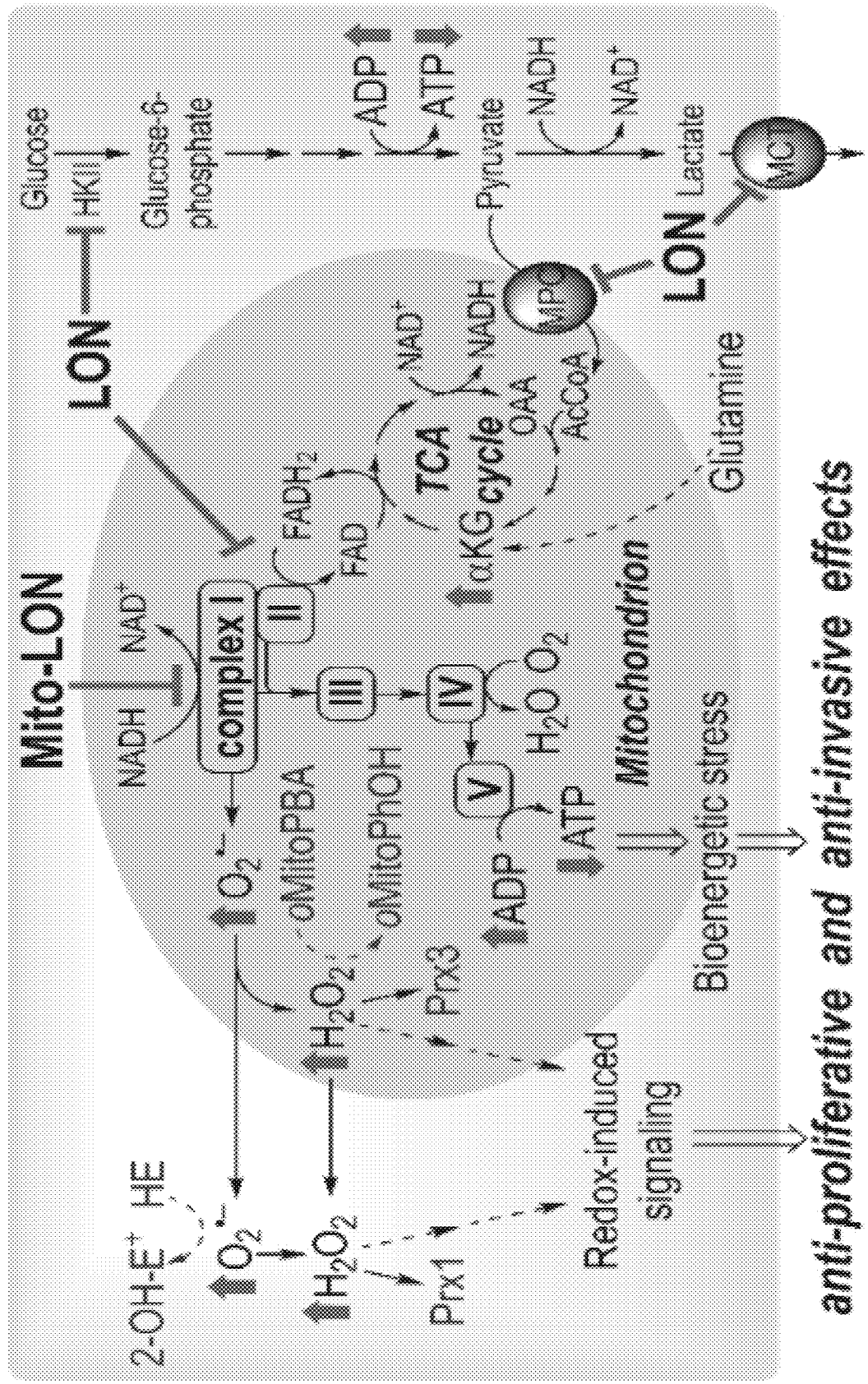
FIG. 11 depicts the targeting of bioenergetic function and redox signaling by LON/Mito-LON. LON inhibits hexokinase II (HKII), monocarboxylate transporter (MCT) and mitochondrial pyruvate carrier (MPC) and complex II. Mito-LON inhibits mitochondrial complex I. Combination of LON and Mito-LON leads to depletion of cellular ATP and stimulation of ROS, leading to inhibition of cell proliferation and invasion. Changes due to the treatment are shown by red (decrease) and green (increase) arrows. Oxidation of HE to 2-OH-E+, oMitoPBA to oMitoPhOH and peroxiredoxins (shown in blue) are used for detection of superoxide, hydrogen peroxide, and compartment-specific redox status, respectively.

FIG. 11 depicts the mechanisms by which Mito-LON may exert enhanced anti-proliferative efficacy in lung cancer cells by inhibiting mitochondrial bioenergetics thereby activating ROS-mediated signaling pathways leading to ACD of cancer cells. FIG. 12 demonstrates that Mito-LON enhanced the formation of 2-hydroxyethidium, a specific marker for $O_2^{\cdot-}$, in lung cancer cells.

Figures 9A, 9B:
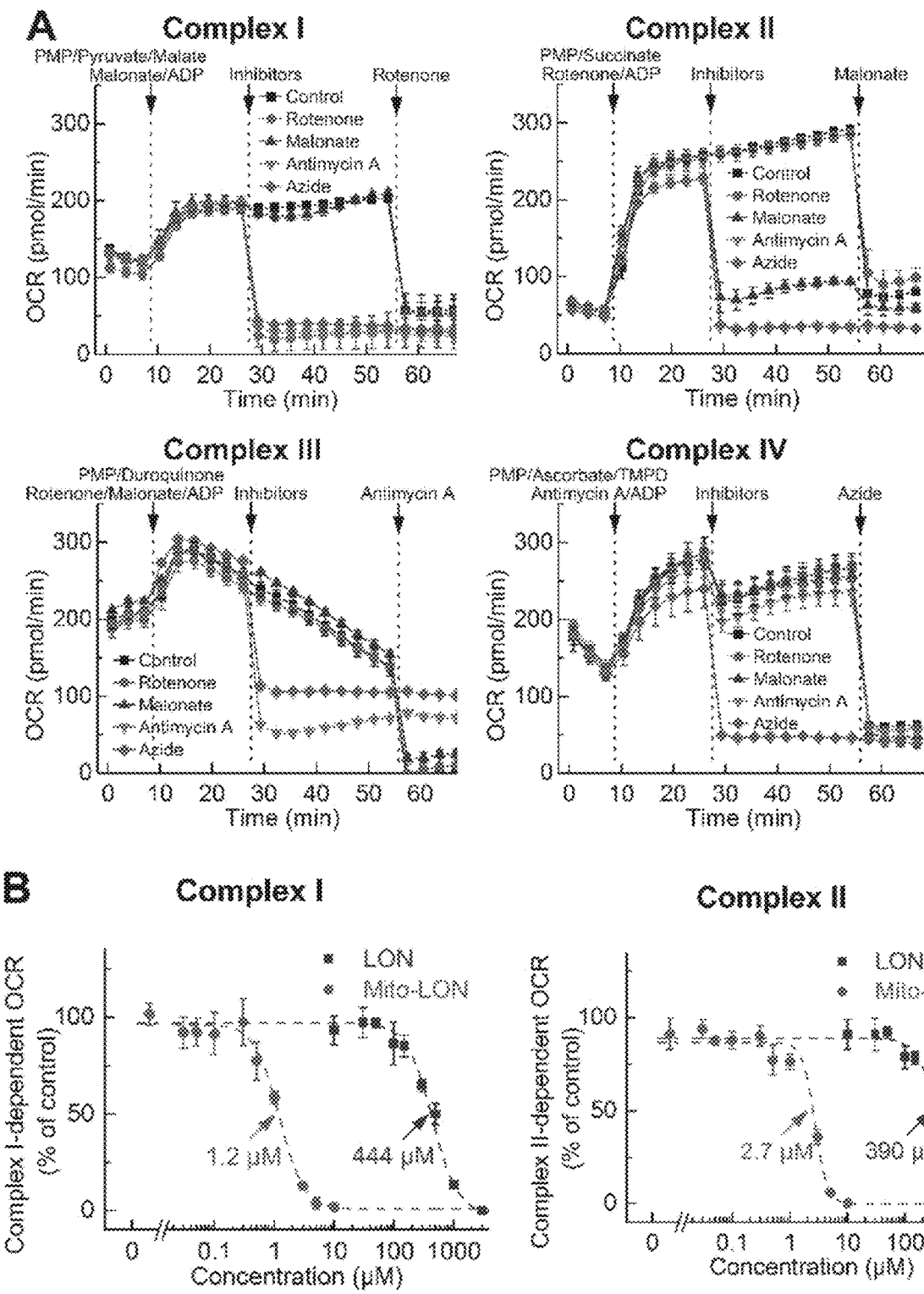
FIGS. 9A-9B demonstrate the effect of LON and Mito-LON on the activity of mitochondrial complexes in H2030BrM3 cells. (A) Effect of mitochondrial substrates and inhibitors on oxygen consumption rate (OCR) in assays of complexes I-IV; (B) Effect of 24-h pretreatment with LON and Mito-LON on OCR in the presence of complex I (top) and complex II (bottom) substrates.
Figure 10:
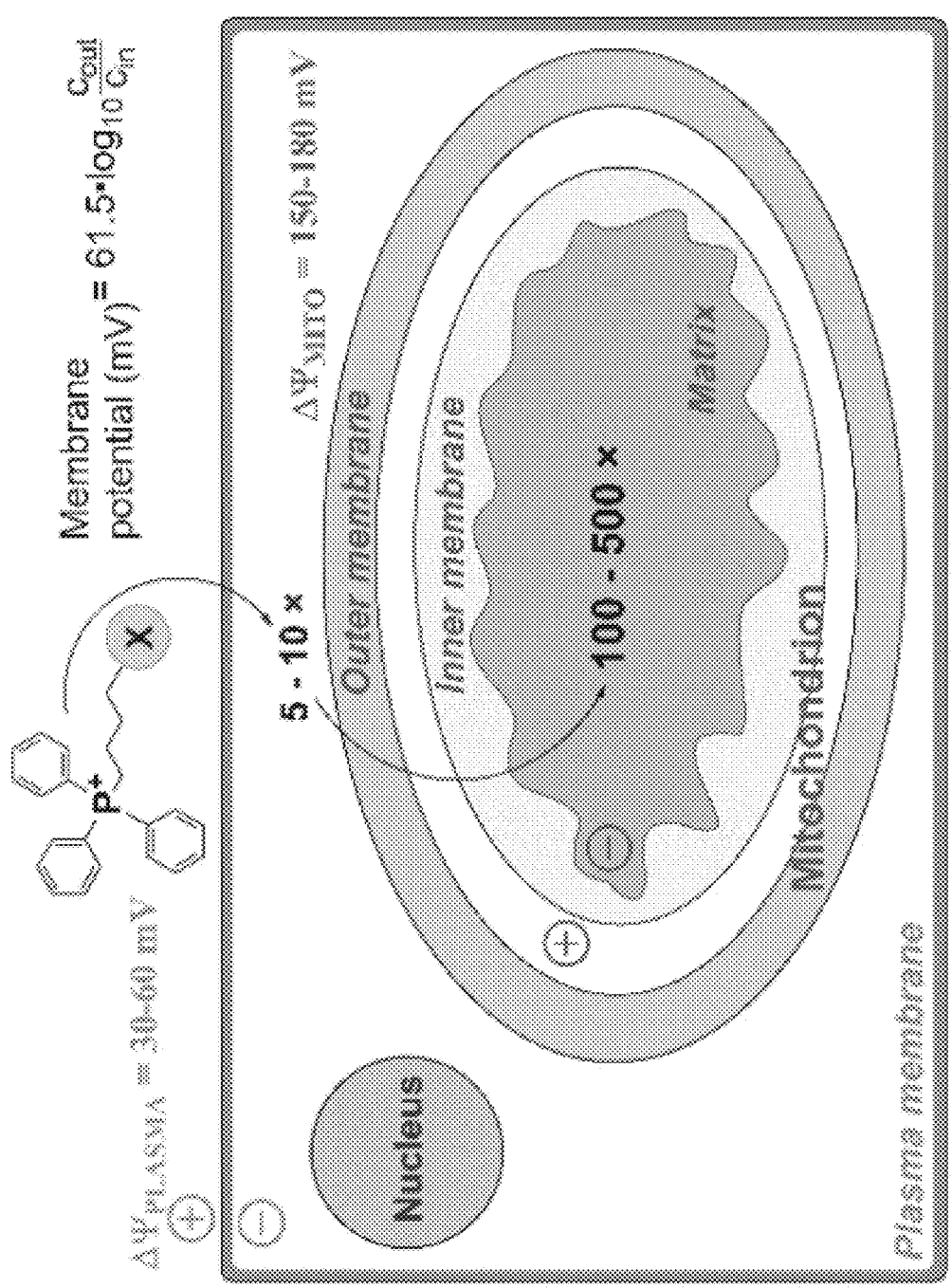
FIG. 10 is a cartoon characterization of uptake of $TPP^+$-linked compounds into cancer cell mitochondria.

LON and Mito-LON inhibit mitochondrial complex I activity. Mito-LON inhibited cellular respiration (oxygen consumption rate, OCR) at >100-fold lower concentration than LON in intact lung cancer cells (FIG. 9). Both basal respiration and the response to mitochondrial stressors (oligomycin, dinitrophenol) were diminished by Mito-LON (not shown). To investigate the mechanism of mitochondrial inhibition, we measured the activity of mitochondrial complexes in H2030BrM3 cells (NSCLC cell line). The cell membrane was permeabilized, and OCR was measured upon addition of substrates and inhibitors of mitochondrial complexes I-IV (FIG. 9A). These studies established the optimal use of permeabilized cells for complex activity assays.[54]

Next, cells were pretreated with LON and Mito-LON for 24 h and experiments performed as in FIG. 9A. Mito-LON is 370- and 144-fold more potent than LON for complexes I and II, respectively (FIG. 9B), which reflects enhanced mitochondrial accumulation of Mito-LON. We hypothesize that inhibition of mitochondrial complexes I and II is the predominant mechanism for antiproliferative effects of Mito-LON on lung cancer cells.

Inhibition of mitochondrial respiration results in increased $O_2^{\cdot-}$ and other oxidants. Mito-LON increased ROS generation in lung cancer cells: both LON (200 µM) and Mito-LON (0.2 µM) induce an increase in intracellular levels of 2-OH-$E^+$, the $O_2^{\cdot-}$-specific product of HE oxidation, in H2030BrM3 cells (FIG. 11). Mito-LON also strongly induced the formation of diethidium ($E^+$-$E^+$), an indicator of other stronger oxidants.[48,55] The ROS induced by Mito-LON are largely within the mitochondria: Mito-LON caused pronounced oxidation of mitochondrial Prx3, without significant effect on cytosolic Prx1 (FIG. 12). Since Prx3 accounts for ~90% of total mitochondrial peroxidase activity, these data indicate that Mito-LON overwhelms the mitochondrial capacity to degrade peroxides.

Figure 14:
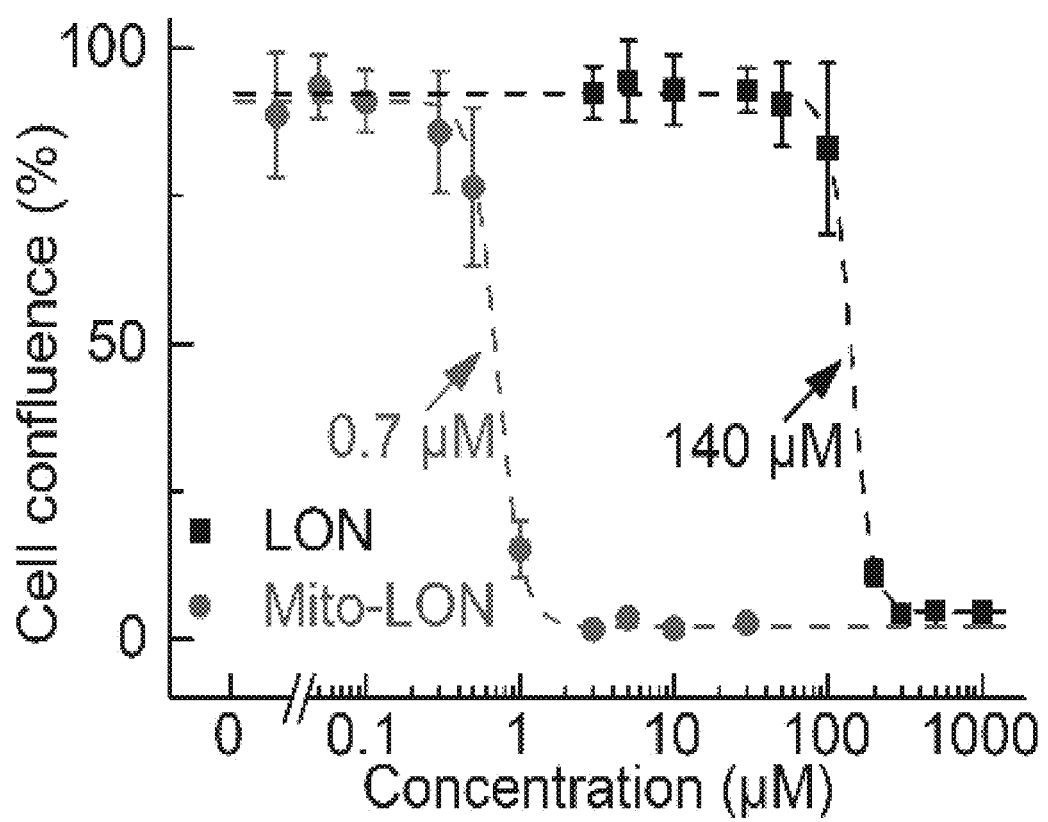
FIG. 14 depicts the effect of LON and Mito-LON on proliferation of H2030BrM3 cells.

Mito-LON is more potent then LON in blocking lung cancer cell growth, and Mito-LON enhances ATP depletion and the antiproliferative effects of LON. Among the different bioenergetic mechanisms proposed for LON, its ability to decrease HK2 levels (see FIG. 17) is among its more sensitive effects ($IC_{50}$~100-150 µM) and is a previously unrecognized mechanism. In contrast, Mito-LON (1.2-2.7 µM) targets mitochondrial complexes I and II (FIG. 9); its mitochondrial effects are supported by the compartment-selective oxidation of mitochondrial Prx3 (FIG. 13). The anti-proliferative effects of Mito-LON and LON were compared in H2030BrM3 cells. Using the IncuCyte™ Live-Cell Imaging Analyzer that provides real-time cell confluence data, we determined that Mito-LON ($IC_{50}$=0.7 µM) inhibits cell proliferation at a 200-fold lower dose than LON ($IC_{50}$=140 µM) (FIG. 14), demonstrating the power of targeting LON to mitochondria. Thus, linking LON to the TPP$^+$ cation promotes mitochondrial accumulation and dramatically improves its effects on mitochondrial complexes I and II leading to significantly increased anti-proliferative activity against lung cancer cells.

Figures 15A, 15B:
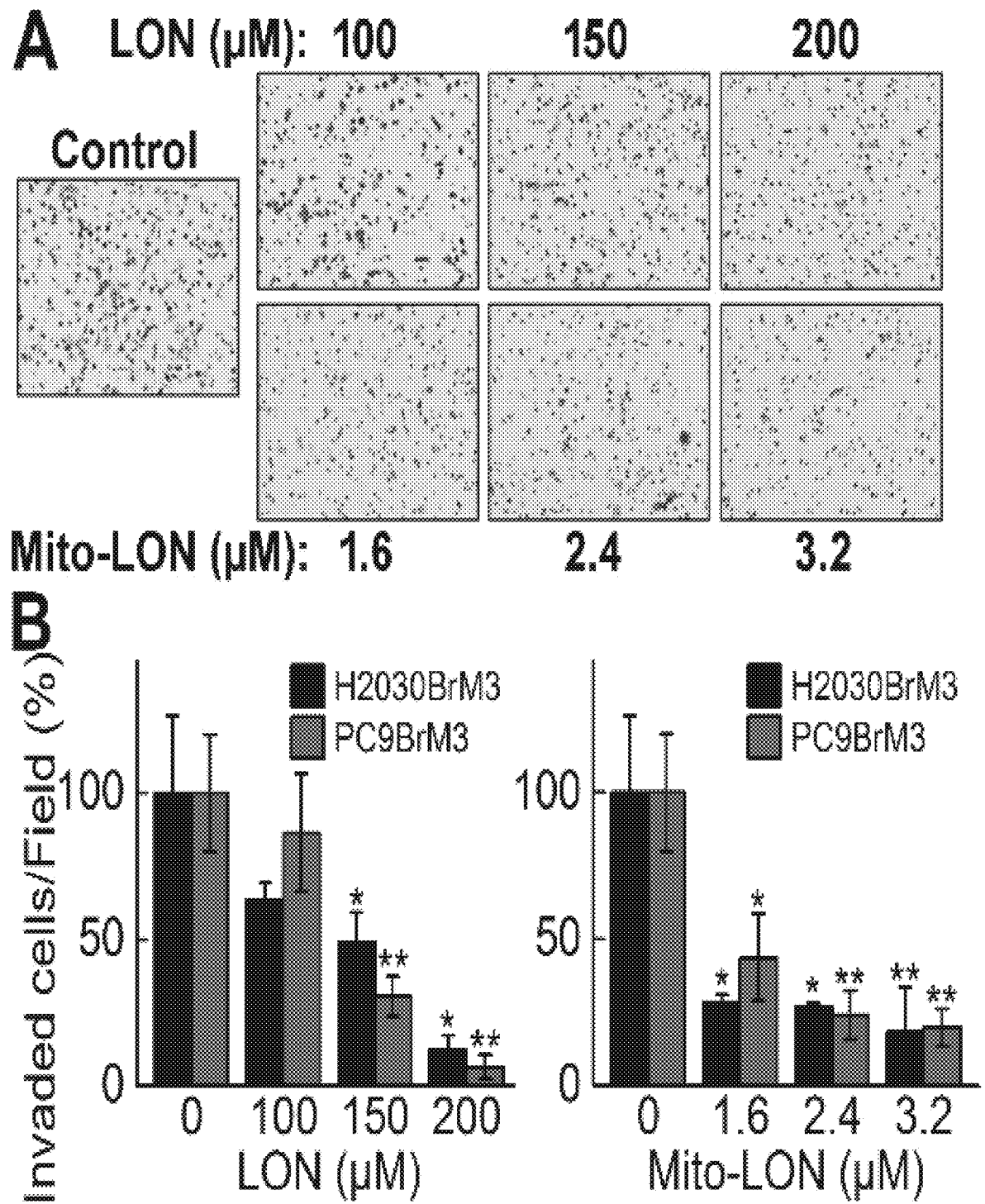
FIGS. 15A-15B depict the effect of LON and Mito-LON on invasion of brain metastatic human lung cancer cells. A. Representative pictures from the transwell assay (H2030BrM3 cells). B. Quantitative analysis data.
Figures 16A, 16B:
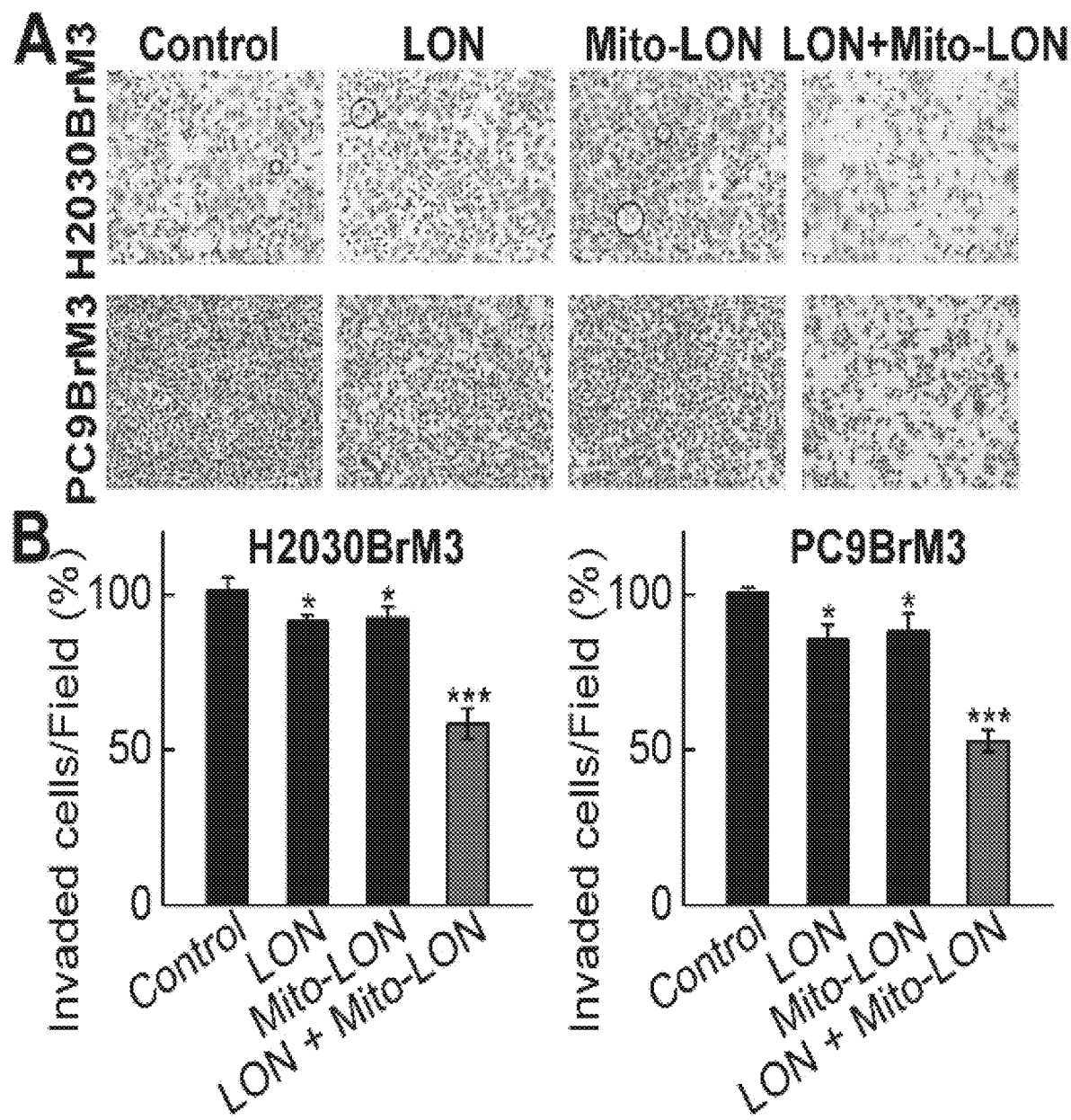
FIGS. 16A-16B depict the effect of the combination of LON and Mito-LON on invasion of brain metastatic human lung cancer cells. A. Representative pictures from the transwell assay. B. Quantitative analysis data. $*p<0.05$; $***p<0.001$.

Mito-LON inhibits migration and invasion of brain metastatic human lung cancer cells. To investigate the potential of Mito-LON and LON for lung cancer metastasis, we first tested its effects in vitro via the Boyden chamber invasion assay using PC9BrM3 and H2030BrM3 brain metastasis lung cancer cell lines. Mito-LON (48 h) was ~100-fold more potent than LON in suppressing invasion (FIG. 15A-B). Also, combining LON (100 µM) with Mito-LON (0.6 µM) led to a significant increase in suppressing invasion, when both agents were used at concentrations having <10% inhibitory effects when used alone (FIG. 16).

Figures 17A, 17B:
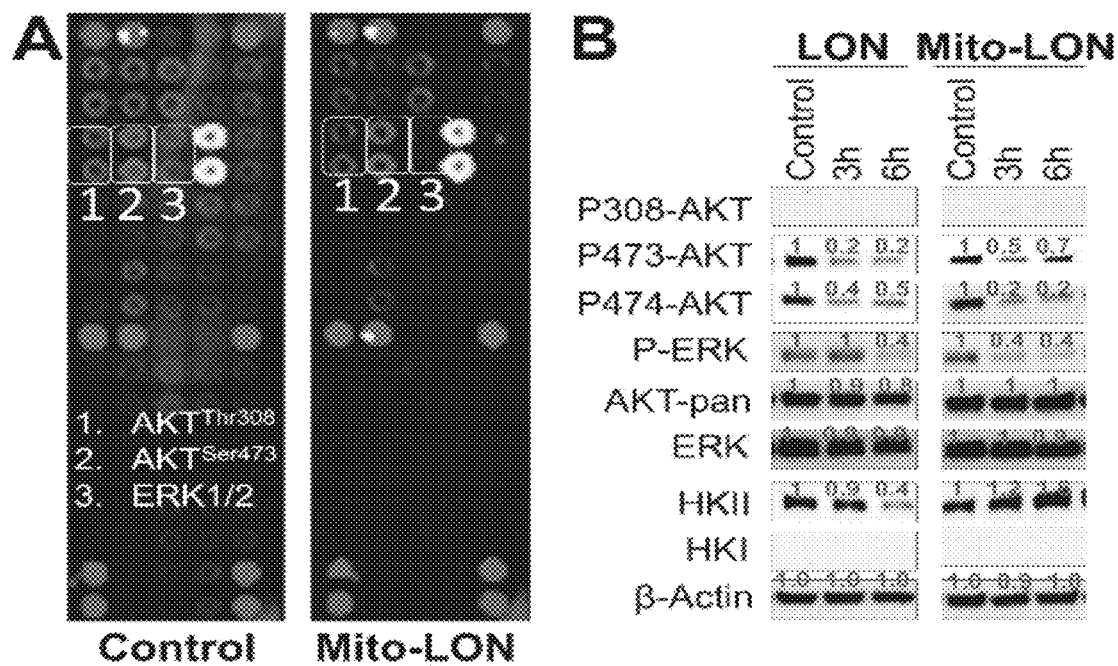
FIGS. 17A-17B depicts the role of ERK1 in anti-proliferative effects of LON and Mito-LON. A, Results of receptor tyrosine kinase assay of H2030BrM3 cells treated with Mito-LON. B, Effect of LON and Mito-LON on AKT and ERK1/2 phosphorylation and expression level of hexokinases in H2030BrM3 cells.

Role of HK2 and additional possible signaling events that contribute to the effects of Mito-LON. LON decreased HK2 levels in both lung cancer lines within 3-6 h (FIG. 17B, PC9BrM3 data not shown), which we propose is a key mechanism by which LON inhibits HK2 activity. LON also decreased HK2 mRNA expression by >80% (not shown). In receptor tyrosine kinase assays to identify additional potential signaling events (FIG. 17A), Mito-LON decreased phosphorylated ERK levels, which was confirmed by Western blots (FIG. 17B). This could contribute to their effects as many cancers have constitutive ERK activation which promotes survival and proliferation, and ERK1 can play an important role in regulating mitochondrial activity, apoptosis, proliferation and migration. Mito-LON also decreased phosphorylated AKT levels which may also contribute to anti-proliferative effects. AKT is another pro-survival factor that is constitutively activated (phosphorylated) in many cancers.

Figure 18:
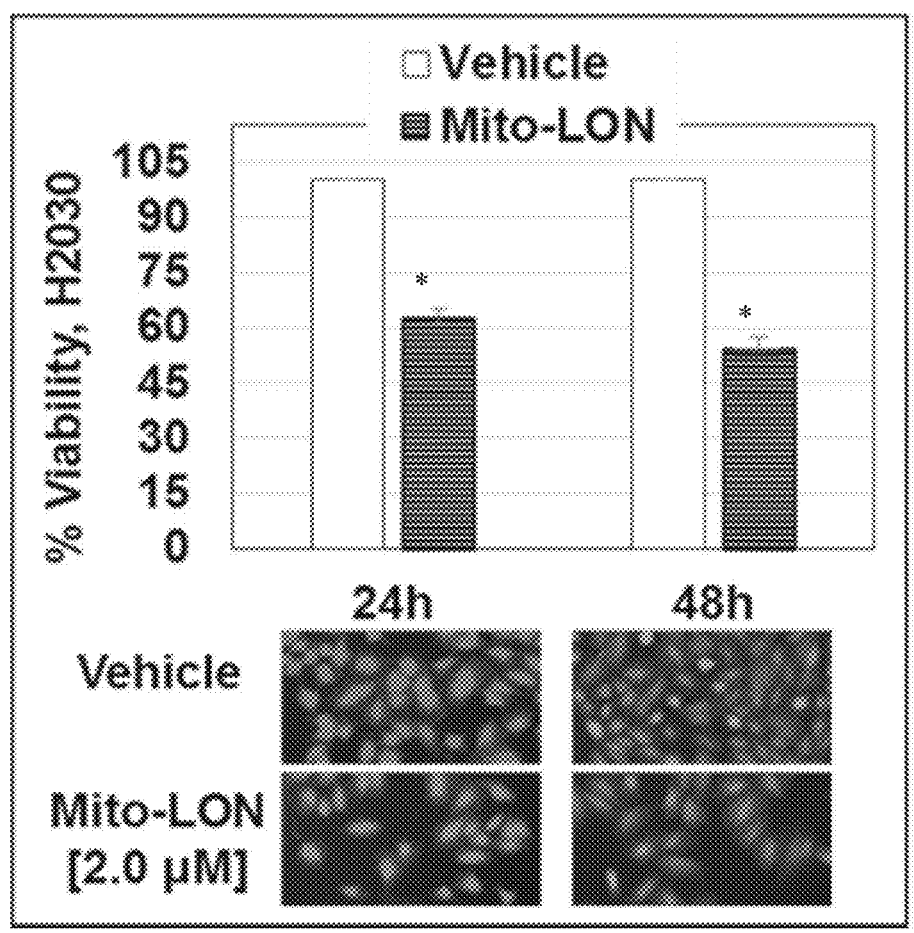
FIG. 18 depicts mito-LON induces lung cancer cell death, $*P<0.05$.

Mito-LON treatment causes cell death of human lung cancer and lung cancer-derived brain metastatic cell lines. Paradoxical roles for autophagy in cancer have been reported for the role of autophagy in cancer. Under conditions of nutrient deprivation autophagy induction can promote cell survival; however, in response to other environmental stressors including ROS generation, autophagy can promote cancer cell death. We treated lung cancer lines (H2030, PC9, H460) and lung cancer-derived brain metastatic lines (H2030BrM3, PC9BrM3) with Mito-LON (1.6, 2.0 or 2.4 µM) and measured cell viability at 24 and 48 h. We determined the LD50 of Mito-LON to be 2.0 µM, with representative results shown in FIG. 18. Mito-LON [2.0 µM] treatment of H2030 cells reduces cell viability about 50% at 48 h based upon Calcein-AM viability stain supporting that Mito-LON significantly reduces cell viability and does not increase lung cancer cell survival.

Mito-LON induces autophagic cell death in human lung cancer cell lines and lung-derived brain metastatic lines. To investigate potential mechanisms underlying Mito-LON's induction of cancer cell death that result from its inhibition of mitochondrial respiration and induction of ROS, we analyzed lysates of cells treated with Mito-LON [2.0 µM] for 0, 6, 24 and 48 h. Lysates were probed for proteins targeting energetics, apoptosis and autophagy, including selective mitophagy markers. Our data (FIG. 19) show Mito-LON treatment [2.0 µM] modulates key autophagy proteins, including specific mitophagy receptors, adaptor proteins and energy sensing molecules in H2030 lung cancer cells and the corresponding brain metastatic line (H2030BrM3). LC3, microtubule-associated protein light chain 3, is critical for cargo recruitment. The LC3 precursor is modified via an ubiquitination-like system generating soluble LC3-I, which is further modified to LC3-II, a membrane-bound phospholipid conjugate upon autophagy induction. LC3-II integrates into the autophagosome membrane and is considered a reliable early marker of autophagy induction. Mito-LON treatment (FIG. 19A) increased levels of LC3-II 1.9 to 4.4-fold across cell lines, with sustained modulation through 48 h. The LC3-interacting region (LIR) serves as a mechanistic basis for selective autophagy, including mitophagy which specifically targets degradation of damaged mitochondria via engagement of adaptor proteins (p62, NBR1, OPTN, BNIP3L). We evaluated the effects of Mito-LON on ubiquitin-binding mitophagy receptors (p62, NDP52, NBR1) which also indicate autophagic flux versus potential impairment of autophagosome turnover. Mito-LON modulated P62 in both cell lines indicating completion of the autophagic degradative process. Changes were consistently bimodal in Mito-LON treated H2030 cells, potentially due to P62's dual role in mitophagy, both in clustering of mitochondria as well as downstream degradation. Mito-LON induced changes in NDP52 paralleled P62 changes. PINK1 was included as an indicator of PINK1-Parkin dependent mitophagy. Basal levels of PINK1 are normally low with increases due to mitochondrial depolarization, damage and ATP alterations, as noted in both cell lines. Beclin1 (BECN1), an autophagy regulator and potential tumor suppressor gene product in multiple cancers, including NSCLC.

Figures 19A, 19B, 19C:
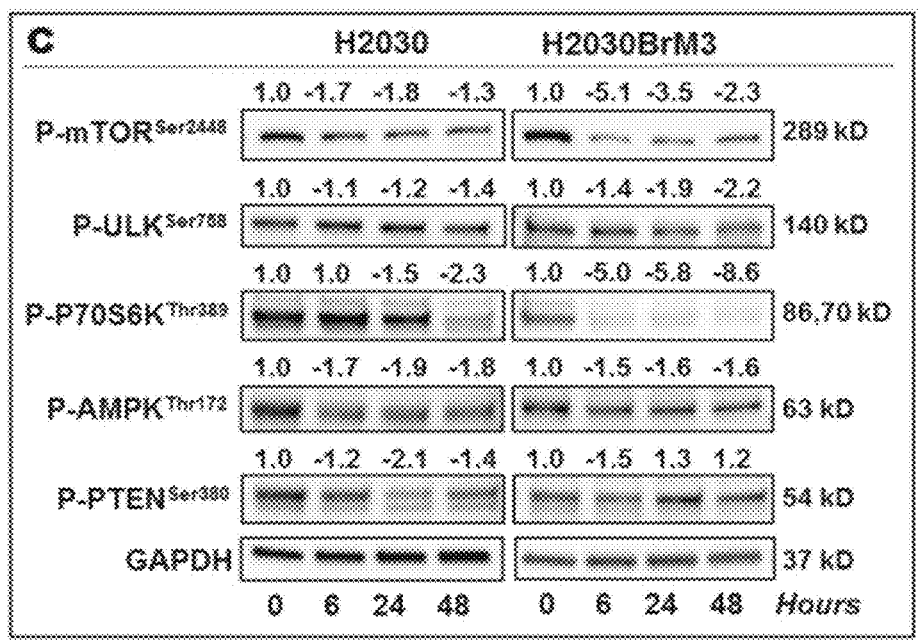
FIGS. 19A-19C depict mito-LON induces autophagy in H2030 and H2030BrM3, a lung-derived metastatic brain cell line over time. 2A, Alterations in autophagy and mitophagy-linked proteins following Mito-LON treatment. 2B, Mito-LON induces autophagic vacuoles in H2030 lung cells; Photomicrographs of H2030 cells treated with Vehicle in a-c or Mito-LON [2.0 µM] in d-f; MDC staining for detection of acidic autophagic vacuoles shown in "c" for Vehicle and "f" for Mito-LON treated H2030 cells, arrows indicate autophagic vacuoles in bright field (b and e) and matched FL MDC labelled cells (c and f). 2C, Mito-LON induced modulation of energy sensing molecules linked to autophagic signaling.

Mito-LON increased Beclin-1 levels in H2030 cells but not in H2030-BrM3 cells (FIG. 19A). Thus, autophagy induction in the lung derived brain metastatic line may be BECN1-independent. H2030BrM3 cells responded uniquely to Mito-LON with increased levels of RAB7 (FIG. 19A), a marker of late autophagy, possibly due to sustained ROS induction. NRF2, a major regulator of cellular stress responses, was not detectable in either cell line. FIG. 19B further supports autophagy induction by Mito-LON. Vehicle treated H2030 cells did not form autophagic vacuoles as illustrated by bright-field photomicrographs (FIG. 19B, panels a & b), and were negative for monodansylcadaverine (MDC) staining (FIG. 19B panel c). In contrast, Mito-LON [2.0 µM] treated H2030 cells showed markedly increased vacuolization characteristic of autophagy (FIG. 19B panels d and e) and stained positive for MDC (FIG. 19B panel f), a marker of autophagic vacuoles based on acidic cellular compartments and lipid partitioning. FIG. 19C shows that Mito-LON deactivates a panel of autophagy-initiating energy-sensing proteins dominating the AKT/mTOR signaling pathway. Specifically, Mito-LON alters phosphorylation events and activating partners in parallel. As an example, P-P70S6K$^{Thr389}$ phosphorylates mTOR$^{Ser2448}$; both reduced in Mito-LON treated cells. Similarly, ULK is activated by AMPK, and both phosphoproteins are decreased by Mito-LON, as is P-PTEN.

Figure 20:
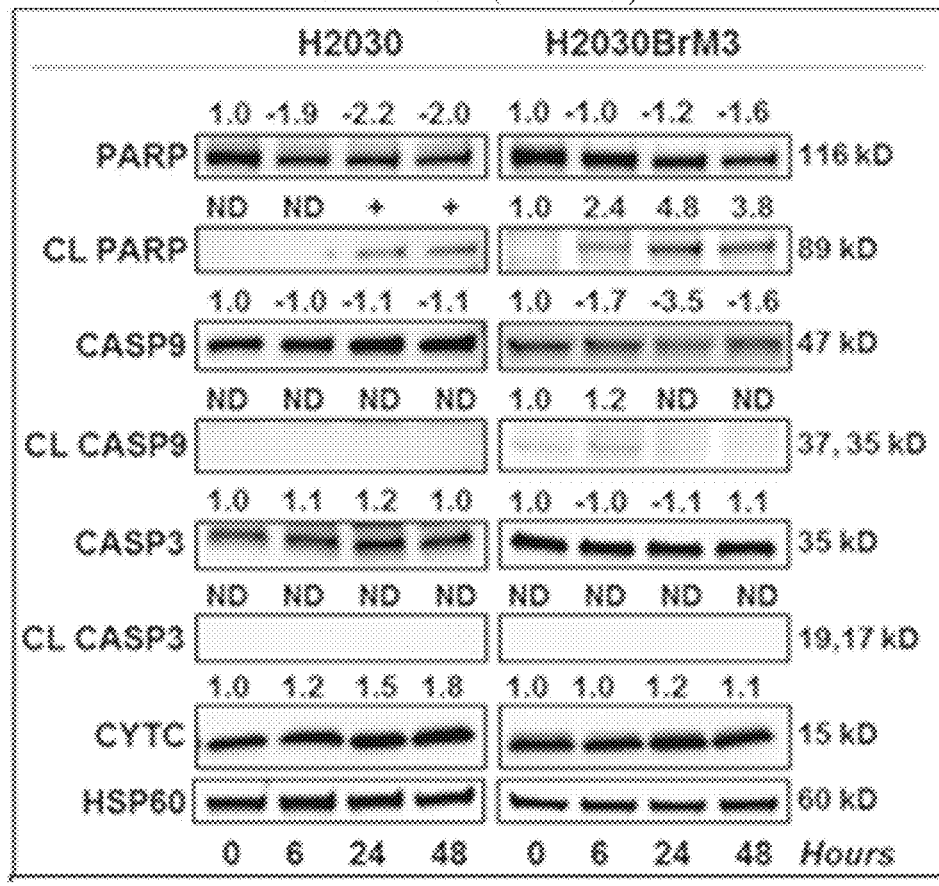
FIG. 20 depicts mito-LON apoptosis in cells.

Mito-LON's effects on inducing apoptosis in human lung cancer cell lines and their lung-derived brain metastatic lines. Results from Mito-LON-treated H2030 and H2030BrM3 cells (FIG. 20) supports cell death induction is mainly via autophagy rather than caspase-dependent apoptosis. Mito-LON treatment resulted in increased levels of cleaved PARP and cytochrome c, but did not induce caspase cleavage.

Figure 21:
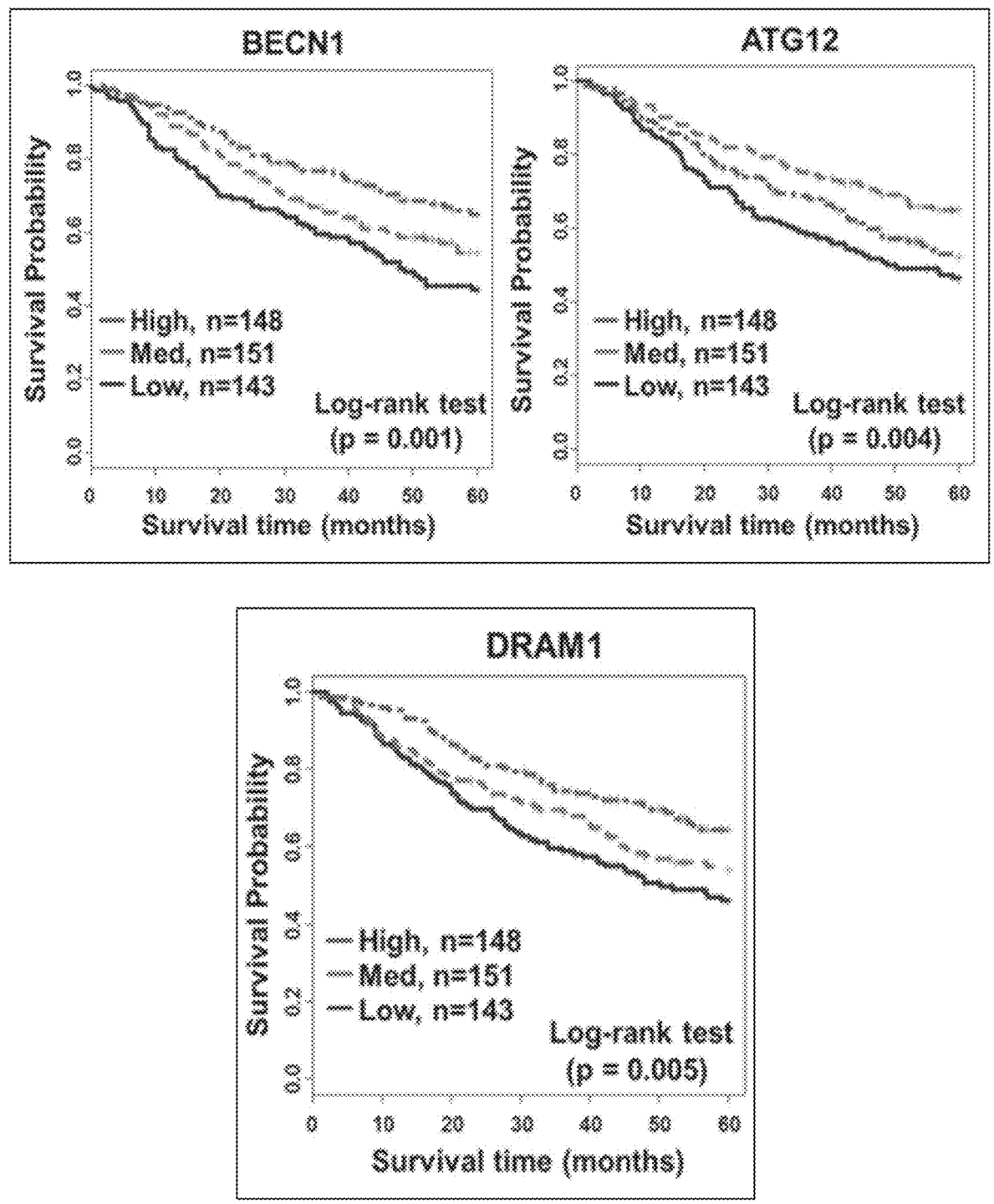
FIG. 21 depict Kaplan-Meier survival curves. High expression of pro-autophagic markers is associated with improved patient survival.

Pro-autophagic markers are linked to improved lung cancer survival. The role of autophagy in human lung cancer progression, metastasis and prognosis is still being unraveled. In a study of >100 patients, high BECN1 expression correlated with well-differentiated non-small cell lung cancers and reduced lymph node metastasis. Additionally, the study reported low BECN1 expression coupled with high p62 expression is significantly associated with shorter patient survival time. We queried our Thoracic Surgery mRNA expression data base (containing 442 lung adenocarcinoma cases) for pro-autophagy markers: BECN1, autophagy related 12 (ATG12), and DNA damage regulated autophagy modulator 1 (DRAM1). In strong agreement with the literature, our data show high expression of each pro-autophagy marker is significantly linked to increased survival among lung adenocarcinoma patients (FIG. 21).

Maximum tolerated dose (MTD) of Mito-LON. We conducted an 8-week toxicology study to evaluate possible toxicity of Mito-LON, especially on neural and muscle cells using a Modified Irwin Screen, developed as a comprehensive observational battery to broadly screen for central nervous system (CNS) effects of agents. Modifications of this test are extensively used in the pharmaceutical industry and in academic research to identify changes in neurological function as a result of agent intoxication, neurotoxicity, or genetic manipulation. The screen used here employs 35 distinct measurements to assess sensorimotor, neurological, and autonomic nervous system function[78]. The effective dose (ED) of Mito-LON is designated as 7.5 µmol/kg based on our preliminary data (FIGS. 24 & 25). We didn't observe any significant differences in body weights (and organ weights) between control and Mito-LON treated mice at up to 50× ED in A/J mice (FIGS. 22A-C) on any of the 35 metrics tested (detecting sensorimotor, neurologic, motor, and autonomic nervous system dysfunction) over 8-weeks treatment (see Appendix). No toxic effects were seen in either neural (frontal cortex and cerebellum) or muscles (skeletal muscles including the soleus, plantaris, gastrocnemius, tibialis anterior and quadriceps) by histopathology as well as liver function (serum levels of AST and ALT) (FIGS. 22B and C). Thus, Mito-LON, at doses up to 50× ED, did not show any toxicity.

Figure 23:
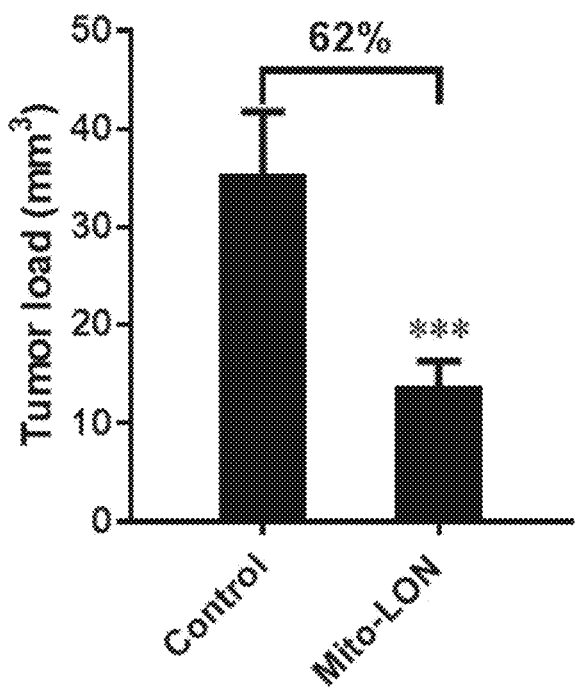
FIG. 23 depicts the effect of mito-LON on VC-induced lung tumorgenesis in A/J mice. Tumor load was measured. Control (n=4) and Mito-LON (n=4). $***P<0.001$.

Preventive efficacy of Mito-LON on vinyl carbamate (VC)-Induced lung carcinogenesis using a post-initiation protocol. We evaluated the preventive efficacy of Mito-LON on the development of VC-induced lung tumors in A/J mice. A post-initiation protocol was used in this study by which administration of Mito-LON was initiated one week after VC. Mito-LON was given via oral gavage at a dose of 15 µmol/kg 5 days/week for 20 weeks. We showed that Mito-LON inhibited VC-induced lung tumor development by 62% in total tumor load (FIG. 23). In addition, we did not observe any body weight changes in Mito-LON treated mice.

Figures 24A, 24B, 24C:
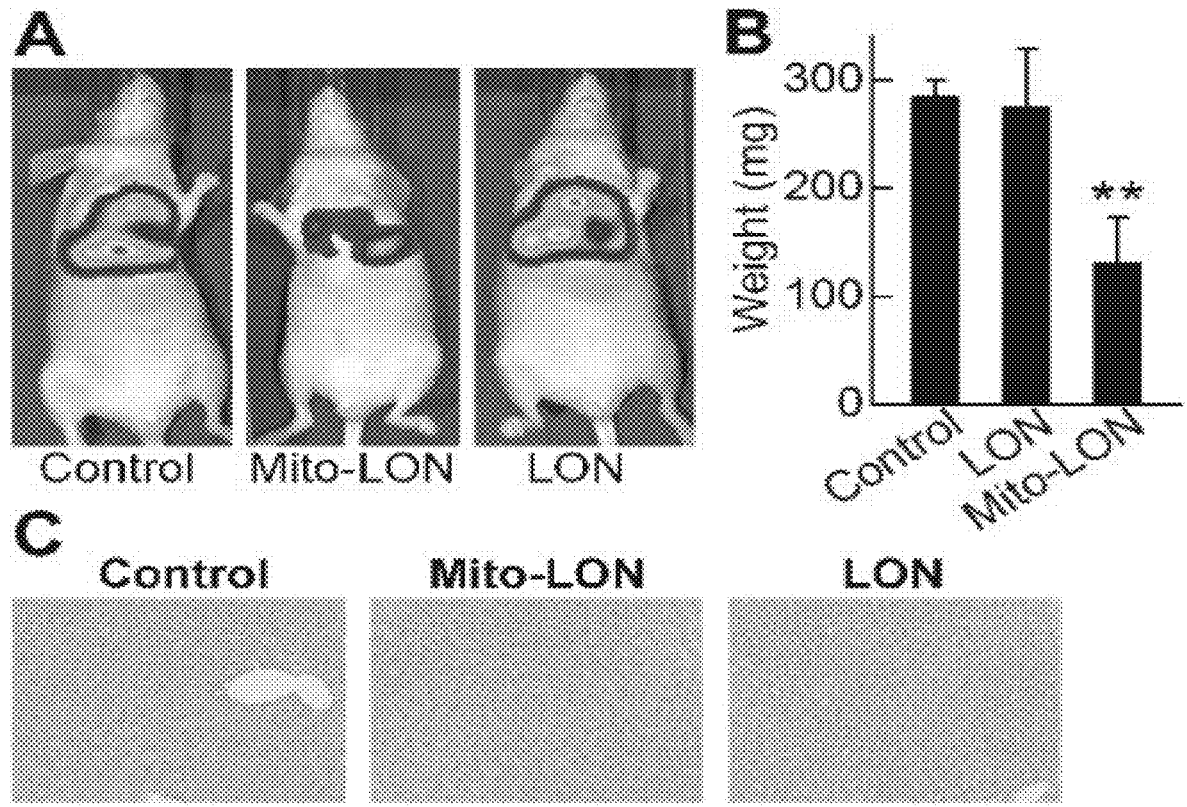
FIGS. 24A-24C depict inhibitor effect of LON or mito-LON on lung tumor growth in orthotopic mice model. (A) Representative Live Images from mice bearing orthotopic J2030-BrM3 lung tumors treated with vehicle (corn oil), LON or Mito-LON, 5 times per week and treatments were continued for 3 weeks. (B) The weight of the mediastinal lymph nodes in control and LON- and Mito-LON-treated mice. (C) Representative images (magnification 10×) of liver tissue-sections after H&E staining.

Inhibitory effects of Mito-LON in an orthotopic lung tumor mouse model. We conducted a pilot study using an orthotopic model of lung adenocarcinoma (H2030BrM3 cells) in nude mice. Cells ($1\times10^6$ cells/50 µg of growth factor-reduced Matrigel in 50 µL of RPMI-1640) were injected into the lung. One week after injection, mice were treated with the same dose of LON or Mito-LON (7.5 µmol/kg), or vehicle (corn oil), by oral gavage 5 times/wk for 3 wks. Equimolar doses were given to illustrate the markedly enhanced potency of Mito-LON relative to LON. LON was not effective as expected as the applied dose (7.5 µmol/kg) which is below that typically used for xenograft studies.[16, 18] In contrast, even at this very low dose, Mito-LON significantly reduced tumor progression (>70%; FIG. 24A) and lymph node metastasis (>50%; FIG. 24B), demonstrating its markedly enhanced potency against both lung cancer progression and metastasis. H&E liver tissue sections (4 µm) from mice treated with Mito-LON (FIG. 24C, blue: nuclear, pink: cytoplasm) showed no histopathologic signs of toxicity (increased mitotic activity, necrophiliac infiltration, fatty changes, centrilobular congestion, or necrosis).

Figures 25A, 25B, 25C:
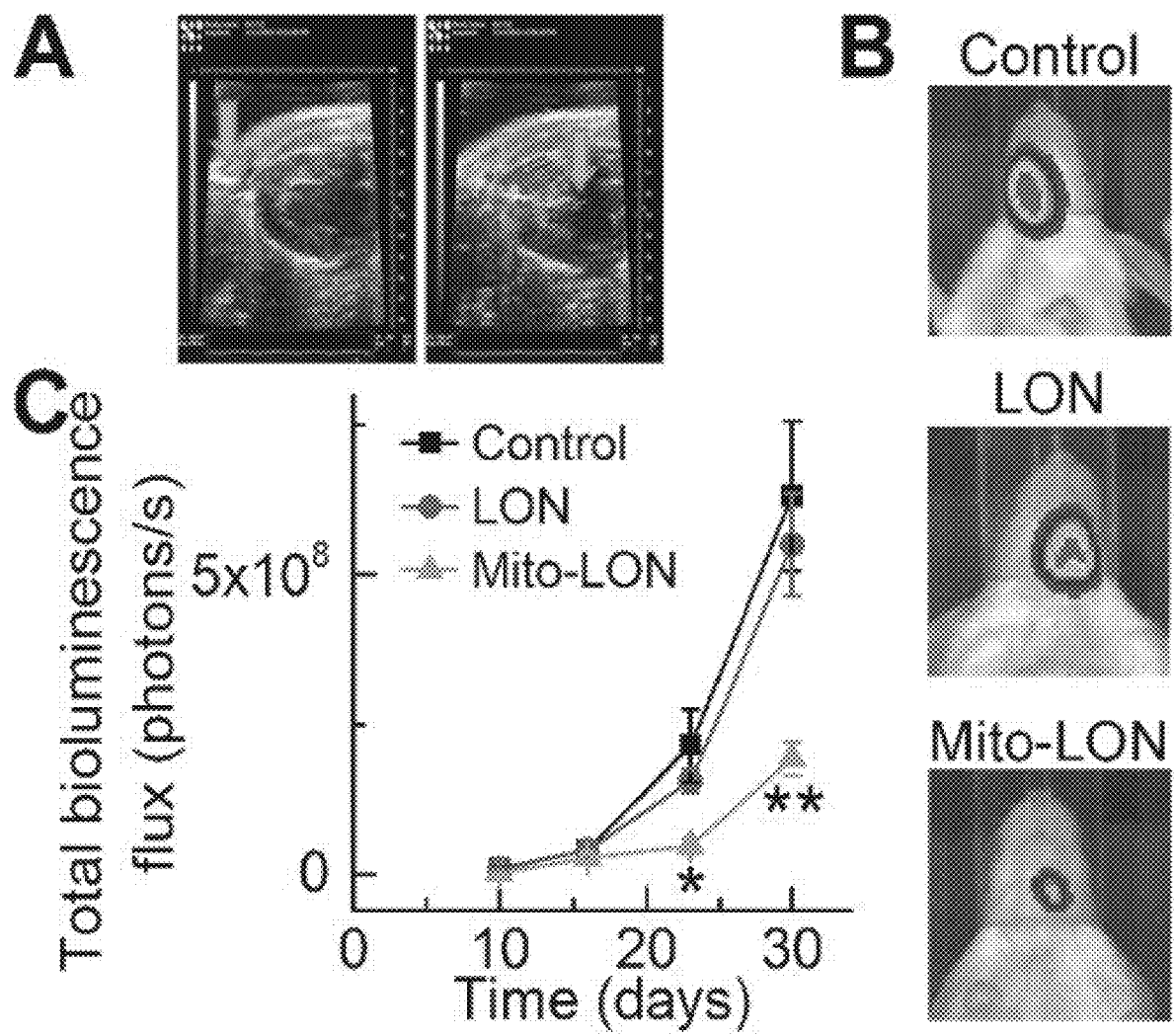
FIGS. 25A-25C depict inhibition of lung cancer brain metastasis by LON and Mito-LON. A. Visualization of needle with the use of high-resolution echocardiography. B. Representative bioluminescence images of brains taken from control, LON and Mito-LON-treated groups. C. Quantitative data for the bioluminescence imaging of the growth of brain metastases. n=6, $*p<0.05$, $**p<0.01$ vs. control.

Mito-LON inhibits lung cancer brain metastasis in Nod/Scid mice. Preliminary experiments assessed the effect of Mito-LON, and its enhanced potency vs. LON, on brain metastasis in Nod/Scid mice in which luciferase-expressing H2030BrM3 cells were injected via intra-cardiac insertion. To ensure the accuracy of injection and precision in the quantity of the cells injected, we used high-resolution echocardiography to guide the needle into the left ventricle. In FIG. 25A, the needle's positioning is clearly discernable. Mice were imaged for firefly luciferase expression (150 µg/g D-luciferin) using an IVIS 100 imaging system at multiple time points post-injection. Regions of interest were defined manually over the brain, and LivingImage and Igor image analysis software were used to determine total photon flux. One day after engrafting the H2030BrM3 cells in arterial circulation (FIG. 19A), LON or Mito-LON (7.5 µmol/kg each) were administered by oral gavage, tumor growth was monitored by bioluminescence, and ex vivo GFP expression and H&E staining were determined at the end point. H2030BrM3 cells rapidly colonized in the cerebrum and cerebellum (FIG. 25B). Mito-LON at this low dose showed significant efficacy in inhibiting brain metastasis of the lung cancer cells (FIG. 25B-C), again illustrating the remarkably greater potency of Mito-LON.

Each publication, patent, and patent publication cited in this disclosure is incorporated in reference herein in its entirety. The present invention is not intended to be limited to the foregoing examples, but encompasses all such modifications and variations as come within the scope of the appended claims.

We claim:
1. A mito-lonidamine compound of formula I:

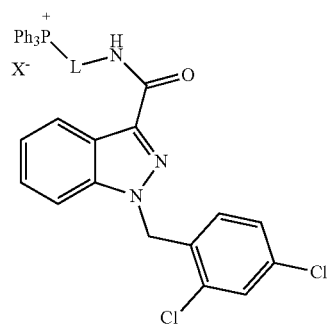

wherein L is a linker selected from an C4-C20 alkyl, an amino acid, benzyl, C2-C20 alkene or PEG, and X is any halogen, 2,2,2-trifluoroacetic acid (TFA) or acetic acid.

2. The mito-lonidamine compound of claim 1, wherein n is selected from an integer from 6 to 20 and X is a halogen of formula Ia

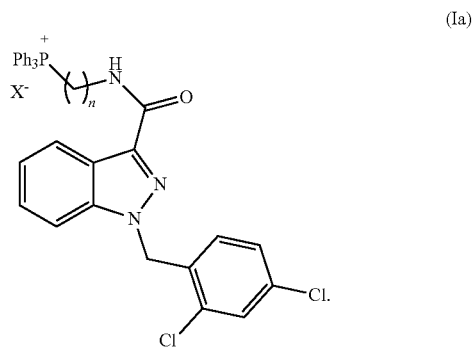

3. The mito-lonidamine compound of claim 2, wherein X is bromine.

4. The mito-lonidamine compound of claim 3, wherein n is 10 (Mito$_{10}$-lonidamine) of formula Ic:

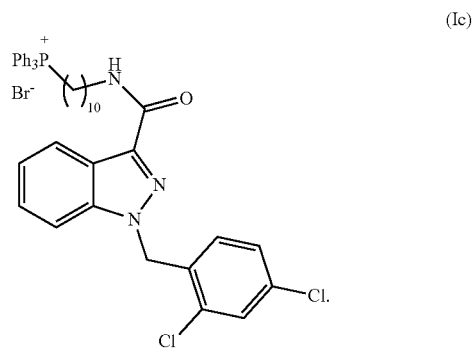

5. A composition comprising a mito-lonidamine compound of claim 1 and a pharmaceutically acceptable carrier.

6. A method of treating cancer in a subject in need thereof, the method comprising administering to the subject an effective amount of a mito-lonidamine compound of formula I:

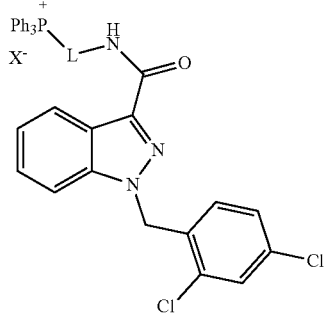

wherein L is a linker selected from an C4-C20 alkyl, an amino acid, benzyl, C2-C20 alkene or PEG,
and X is any halogen, 2,2,2-trifluoroacetic acid (TFA) or acetic acid.

7. The method of claim 6, wherein the mito-lonidamine compound is mito-lonidamine of formula Ia:

(Ia)

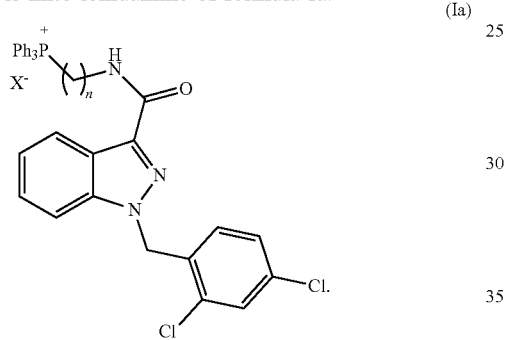

wherein n is selected from an integer of 6 to 20 and X is a halogen.

8. The method of claim 6, wherein the cancer is pancreatic cancer.

9. The method of claim 6, wherein the cancer is non-small cell lung cancer.

10. A method of reducing cancer cell growth in a subject, the method comprising administering to the subject an effective amount of a mito-lonidamine compound of formula I:

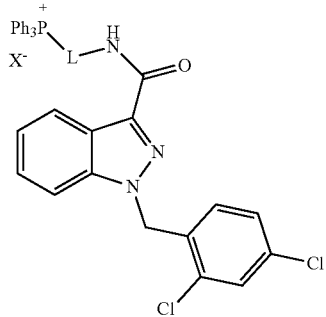

wherein L is a linker selected from an C4-C20 alkyl, an amino acid, benzyl, C2-C20 alkene or PEG,
and X is any halogen, 2,2,2-trifluoroacetic acid (TFA) or acetic acid.

11. The method of claim 10, wherein the mito-lonidamine compound is a compound of formula Ia:

(Ia)

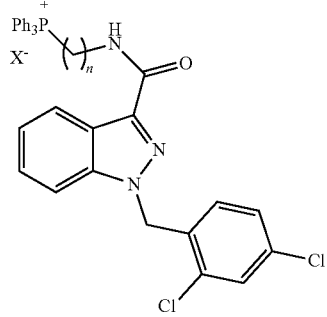

wherein n is selected from an integer from 6 to 20 and X is a halogen.

12. A method of reducing metastasis of a cancer in a subject, the method comprising administering to the subject an effective amount of a mito-lonidamine compound of claim 1 to reduce metastasis in the subject.

13. The method of claim 12, wherein the mito-lonidamine compound is Mito-lonidamine of formula Ia (Ia)

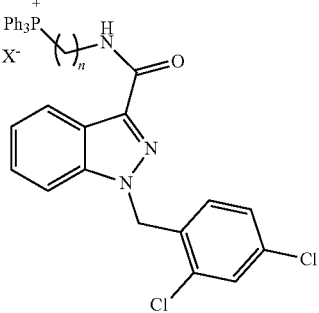

wherein n is selected from an integer from 6 to 20 and X is a halogen.

14. The method of claim 12, wherein the mito-lonidamine is $mito_{10}$-lonidamine of formula Ic:

(Ic)

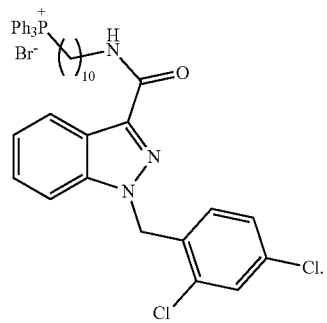

15. The method of claim 10, wherein the cancer is non-small cell lung cancer.

16. The method of claim 12, wherein the metastasis is brain metastasis.

17. The method of claim 6, wherein the subject is human.

18. The method of claim 6, wherein the cancer is non-small cell lung cancer.

19. The mito-lonidamine compound of claim 1, wherein L is a C8-C20 alkyl.

* * * * *